(12) United States Patent
Yamamoto

(10) Patent No.: US 9,114,402 B2
(45) Date of Patent: Aug. 25, 2015

(54) CHANNEL DEVICE AND SAMPLE TREATMENT APPARATUS INCLUDING THE SAME

(75) Inventor: Takatoki Yamamoto, Tokyo (JP)

(73) Assignee: Japan Science And Technology Agency, Kawaguchi-Shi (JP)

( * ) Notice: Subject to any disclaimer, the term of this patent is extended or adjusted under 35 U.S.C. 154(b) by 480 days.

(21) Appl. No.: 13/513,331

(22) PCT Filed: Jul. 26, 2010

(86) PCT No.: PCT/JP2010/062497
§ 371 (c)(1),
(2), (4) Date: Aug. 10, 2012

(87) PCT Pub. No.: WO2011/067961
PCT Pub. Date: Jun. 9, 2011

(65) Prior Publication Data
US 2012/0298511 A1  Nov. 29, 2012

(30) Foreign Application Priority Data

Dec. 2, 2009 (JP) ................................ 2009-274921
Dec. 25, 2009 (JP) ................................ 2009-293960

(51) Int. Cl.
*B03C 5/02* (2006.01)
*B01L 3/00* (2006.01)
*G01N 15/10* (2006.01)

(52) U.S. Cl.
CPC ........... *B03C 5/026* (2013.01); *B01L 3/502761* (2013.01); *G01N 15/1031* (2013.01);
(Continued)

(58) Field of Classification Search
CPC ............... B03C 5/026; B03C 2201/26; G01N 15/1031; G01N 15/1056; B01L 2/502761; B01L 2400/0415; B01L 2300/0896; B01L 2300/0864; B01L 2300/0652; B01L 2300/0645
USPC ...................... 204/403.01, 406, 407; 205/792
See application file for complete search history.

(56) References Cited

U.S. PATENT DOCUMENTS

| 2006/0275911 A1 | 12/2006 | Wang et al. |
| 2008/0251382 A1 | 10/2008 | Han et al. |
| 2009/0023146 A1 | 1/2009 | Harnack et al. |

FOREIGN PATENT DOCUMENTS

| JP | 2003-510034 A | 3/2003 |
| JP | 2005-532545 A | 10/2005 |

(Continued)

OTHER PUBLICATIONS

A machine translation of WO 2008/041718.*

(Continued)

*Primary Examiner* — J. Christopher Ball
(74) *Attorney, Agent, or Firm* — Foley & Lardner LLP

(57) ABSTRACT

A channel device including a nanosize channel through which single molecule flows, at least one electrode pair arranged near the nanosize channel, and an AC power source that applies an AC voltage to the electrodes. This channel device is useful for identifying molecules one by one. Furthermore, a channel device including a nanosize channel through which single molecule flows, a branching portion, and a plurality of branching channels, wherein (i) an electrode pair is arranged near the nanosize channel so as to sandwich the nanosize channel between the electrodes, or (ii) one electrode of the electrode pair is located near the nanosize channel, whereas the other is arranged near the branching channels. This channel device is useful for separating single molecule. The present channel device achieves identification or separation at an accuracy of 100% in principle. A sample treatment apparatus according to present invention includes a channel device, a measurement section, and an arithmetic processing section. The measurement section applies a voltage (DC or AC) to between electrodes of an electrode pair installed in the nanosize channel, and measures an electric signal when single molecule passes between the electrodes to identify the molecule (see FIG. 1B).

36 Claims, 25 Drawing Sheets

(52) U.S. Cl.
CPC ..... *G01N15/1056* (2013.01); *B01L 2200/0652* (2013.01); *B01L 2300/0645* (2013.01); *B01L 2300/0864* (2013.01); *B01L 2300/0896* (2013.01); *B01L 2400/0415* (2013.01); *B03C 2201/26* (2013.01)

(56) References Cited

FOREIGN PATENT DOCUMENTS

| | | |
|---|---|---|
| JP | 2006-023209 A | 1/2006 |
| JP | 2008-532733 A | 8/2008 |
| JP | 2008-536124 A | 9/2009 |
| WO | WO-01/18246 A1 | 3/2001 |
| WO | WO 2004/005910 A1 | 1/2004 |
| WO | WO-2006/081270 A2 | 8/2006 |
| WO | WO-2007/084163 A2 | 7/2007 |
| WO | WO-2008/079169 A2 | 7/2008 |
| WO | WO-2008/041718 A1 | 4/2010 |

OTHER PUBLICATIONS

International Search Report PCT/JP2010/062497 dated Nov. 2, 2010.

* cited by examiner

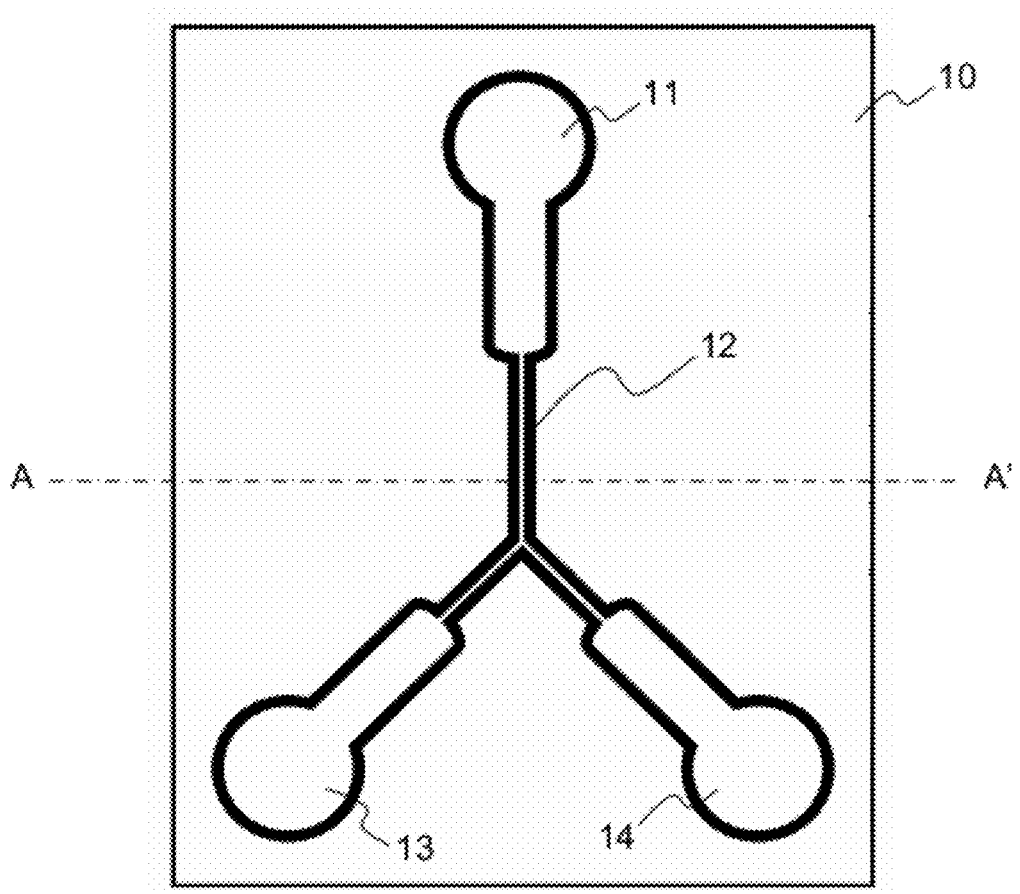

Fig. 11
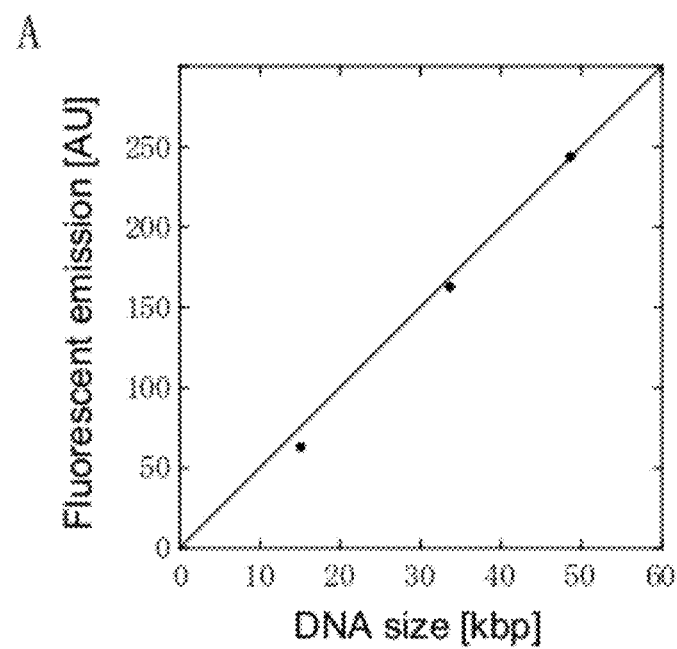
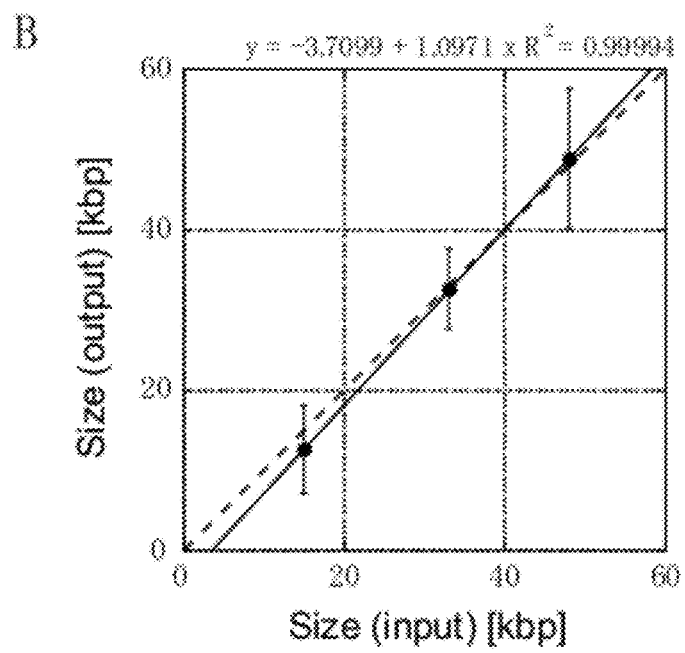

Fig. 16
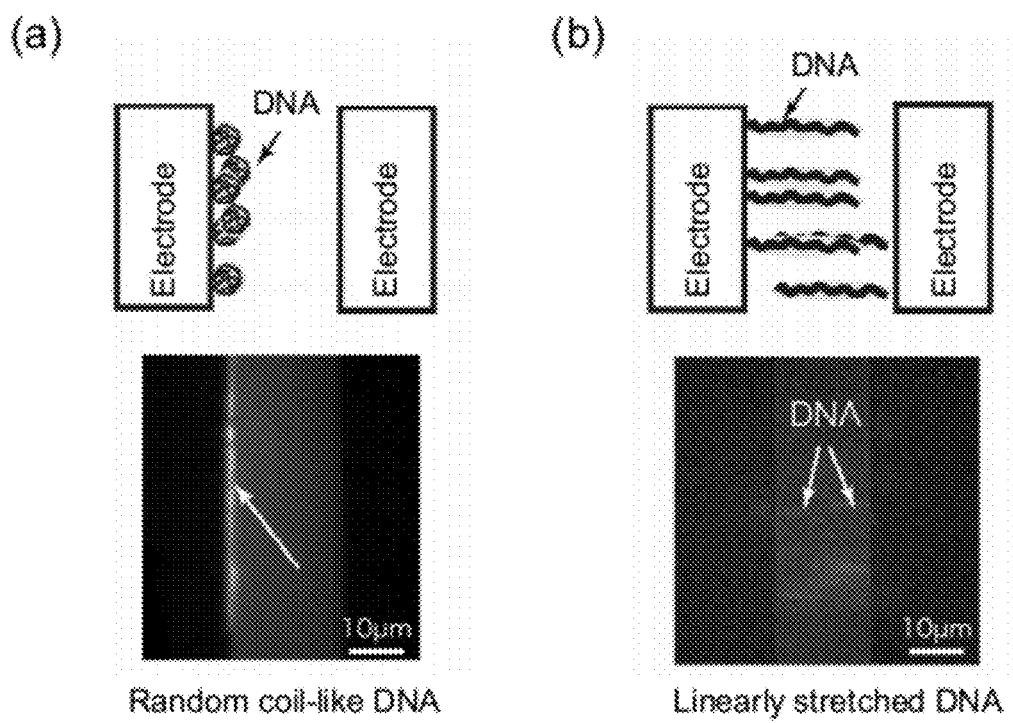
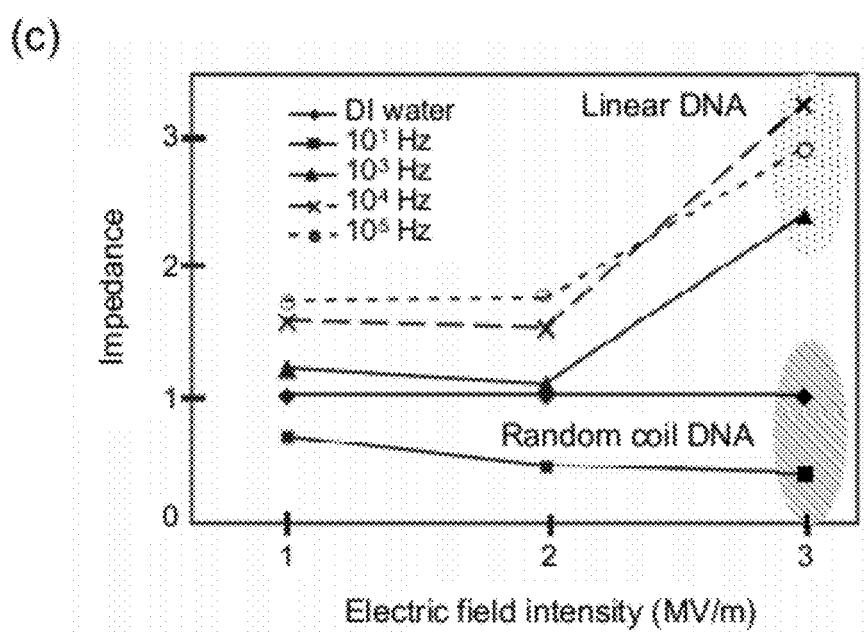

Fig. 20
(A)
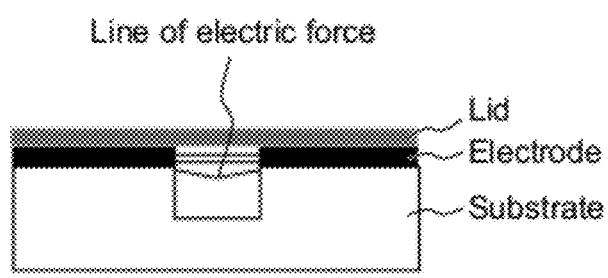
Pattern 1
(B)
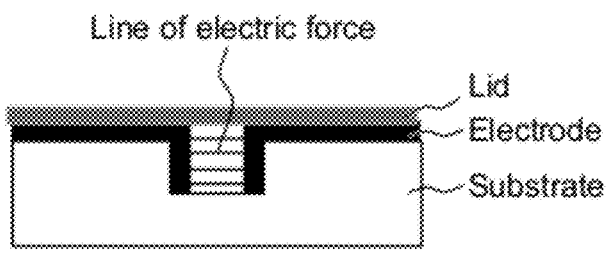
Pattern 2

Fig. 21
(A) 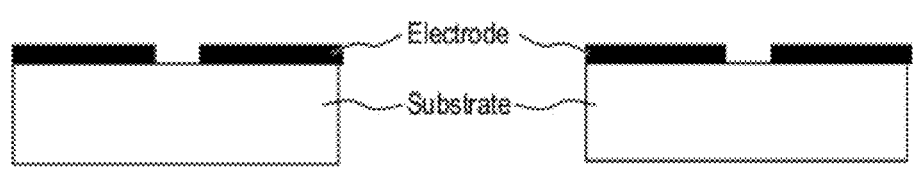
(B) 
(C) 
(D) 

Fig. 22
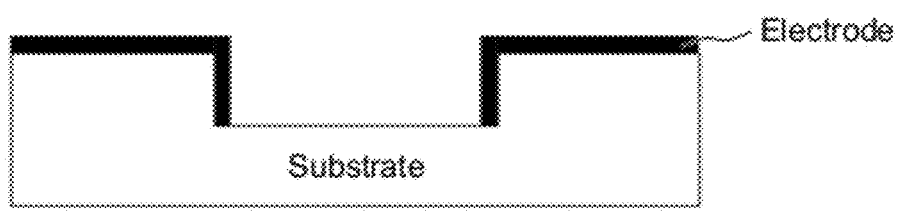
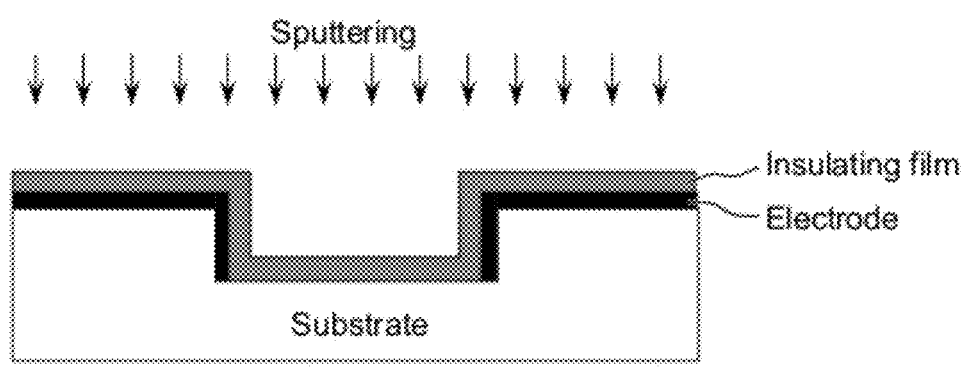

Fig. 23
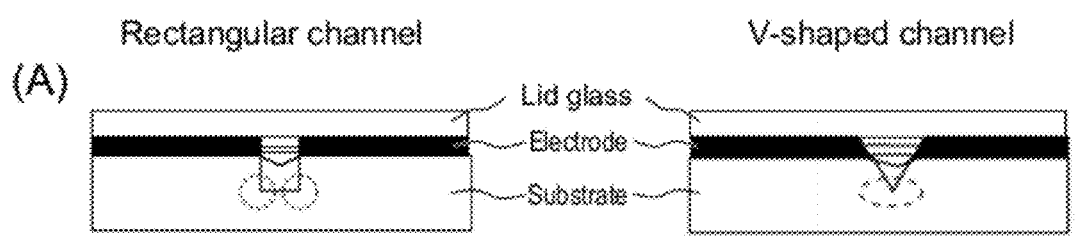
Comparison of range for electric measurement
Comparison of position where molecule flows Fig. 24
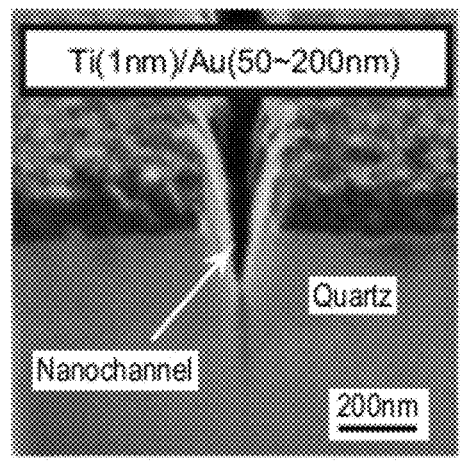
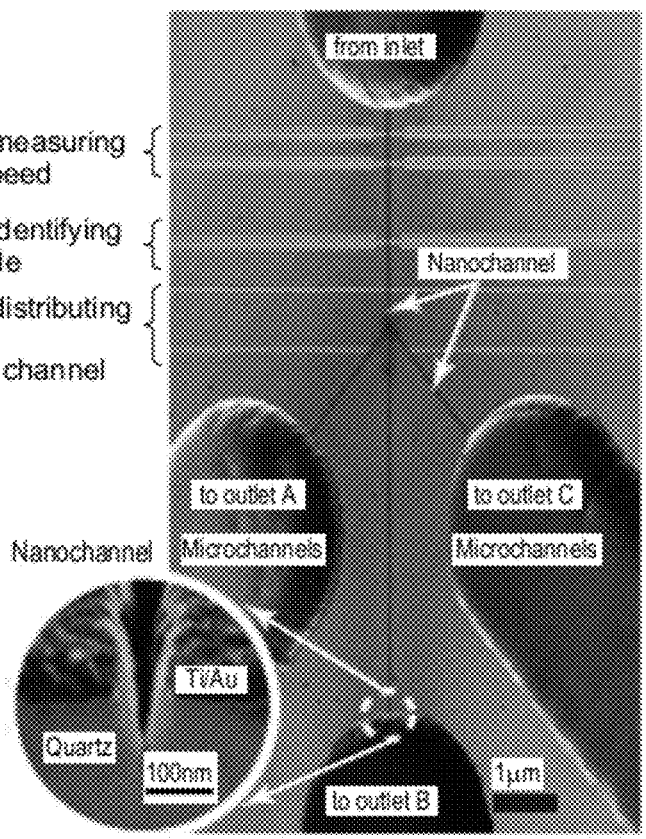

CHANNEL DEVICE AND SAMPLE TREATMENT APPARATUS INCLUDING THE SAME

TECHNICAL FIELD

The present invention relates to a channel device and a sample (the "sample" as used herein refers to a sample liquid) treatment apparatus including the same. For example, the present invention can carry out one-by-one identification (including specification, sensing, detection, and measurement) or separation (including sorting) of molecules contained in the sample.

BACKGROUND ART

A chromatography technique has been known to be used to separate desired molecules from a sample. This method repeats adsorption and desorption of molecules to and from what is called separation carriers to separate the molecules from one another based on a difference in mobility during a stochastic process (see, for example, Patent Literature 1). More specifically, for example, a sample containing various molecules is allowed to flow through a cylinder with porous particles (separation carriers) filled therein (a unit with such separation carriers filled therein is referred to as a "column"). Then, molecules smaller than pores in the separation carriers can enter the pores, but molecules larger than the pores cannot enter the pores and pass by the separation carriers. That is, the molecules smaller than the pores flow into and out of the pores and thus migrate at a reduced speed. The molecules larger than the pores cannot enter the pores and thus migrate fast. The molecules are separated from one another based on the difference in migration speed.

CITATION LIST

Patent Literature

Patent Literature 1: JP Patent Publication (Kokai) No. 2007-279028

SUMMARY OF THE INVENTION

Technical Problem

However, a method using such conventional chromatography as disclosed in Patent Literature 1 in principle (even under ideal conditions) fails to achieve 100% separation of the desired molecules. This is because the molecules undergo Brownian motion and accidentally flow into and out of the pores in the separation carriers (this accidentalness relates to the stochastic process). This is also because molecules that are similar to one another in size similarly flow into and out of the pores and are thus difficult to be distinguished from one another. Moreover, the conventional method can separate several of many types of molecules from one another but cannot exhaustively separate all the types of molecules from one another.

The present invention provides a technique for enabling the one-by-one identification or separation based on a principle that is completely different from the above-described mechanical principle that relies on a size of pores.

Solution to Problem

Processing techniques have recently improved to provide channels with a cross section of a nanometer size, that is, nanometer size channels.

The present inventors are separately engaged in molecules of a nanometer size, for example, biomolecules, and have conceived the idea that if the nanometer size channel and the biomolecule are combined together such that a "sample containing molecules of a nanometer size" is allowed to flow through a nanometer size channel, then each of the molecules can flow through the nanometer size channel. Moreover, the present inventors have focused on the electrical nature of the molecules. The electrical nature includes that of molecules exhibited when the molecules are electrically stimulated or during the electric stimulation.

As a result, the present inventors have conceived a channel device with at least one electrode pair arranged near a nanometer size channel through which single molecule flows (the nanometer size channel is hereinafter sometimes simply referred to as a nanosize channel or a nanochannel). Based on this idea, the present inventors have invented a channel device including a nanosize channel through which single molecule flows, and at least one electrode pair arranged in or/and near the nanosize channel, and an AC power source that applies an AC voltage to the electrodes (first basic invention).

FIG. 1A is a schematic plan view showing a channel device with the simplest configuration. In FIG. 1A, a nanochannel 12 is viewed from above. The nanochannel 12 is surrounded by a substrate. The nanochannel may be formed on the substrate as shown in FIG. 1A or inside a pipe, without limitation. An AC voltage is applied to each of molecules by an AC power source (AS) via a pair of electrodes E1 and E2. As a result, the electrical nature of molecules flowing one after another through the nanochannel can be measured. This allows the molecules to be identified one by one. In this case, the use of the AC voltage enables highly sensitive and accurate identification. The identification has a broad meaning and includes sensing of the state of the molecule, for example, the conformation of the module and dynamic changes therein (dynamic state).

Once single molecule can be identified (sensed), the molecule can be specifically caught at an outlet of the channel. Thus, the channel device according to the present invention can be used to separate only particular molecules from a sample.

Moreover, molecules, when subjected to electric stimulation (an electric signal), may exhibit dynamically specific behavior. In that case, the channel device according to the present invention is provided with a plurality of branching channels (having a nanometer size or larger) at the outlet thereof, and each molecule flowing through each of the channels is subjected to particular electric stimulation. Then, for example, a molecule of a first type exhibits first dynamic behavior, and as a result, is guided through a first branching channel. For example, a molecule of second type exhibits a second dynamic behavior, and as a result, is guided through a second branching channel.

Thus, the present invention provides a channel device including a nanochannel through which single molecule flows, a branching portion, and a plurality of branching channels (a second basic invention). The branching channel ranges from a nanometer order to a micrometer order in cross-sectional size.

FIG. 1B is a schematic plan view showing a channel device with a plurality of branching channels 12a and 12b. The channel device is useful for separation. A nanochannel 12 is viewed from above. The nanochannel 12 is surrounded by a substrate. An outlet side of the nanochannel 12 (the right side of FIG. 1B) branches into the two branching channels 12a and 12b via a branching portion. The channel as a whole is Y-shaped. In this case, an electrode pair is i) electrodes E1 and E2 with the nanochannel 12 located therebetween or ii) the electrode E1 located near the nanochannel 12 and an electrode E3 located at the branching channel, or iii) the electrode E2 located near the nanochannel 12 and an electrode E4 located at the branching channel.

A predetermined voltage is applied to between paired electrodes (a pair of E2 and E4 or a pair of E2 and E1) to electrically stimulate a predetermined molecule M contained in a sample. Then, the molecule M is guided to the branching channel 12b.

Moreover, the present invention provides a channel device including a nanochannel through which single molecule flows, a branching portion, and a plurality of branching channels, and i) an electrode pair is arranged near the nanochannel so as to sandwich the nanochannel between the electrodes, or ii) one electrode of the electrode pair is located near the nanochannel 12, whereas the other is arranged near the branching channel (a third basic invention).

The channel device with the branching channels described above is, for example, useful for separation. However, in another usage, a sample is allowed to flow from the branching channel toward the nanochannel.

Essentially, the molecule M can be drawn (or repelled) toward a "certain electrode". Thus, when the molecule M flows, for example, from left to right in FIG. 1B, drawing the molecule M toward the electrode E2 (or the electrode E4) allows the molecule M to be guided to the lower branching channel 12b. Drawing the molecule M toward the electrode E1 (or the electrode E3) allows the molecule M to be guided to the upper branching channel 12a. In this case, electrophoresis can be caused in which the molecule M is guided by a Coulomb's force utilizing the polarity (+ or −) of the molecule. However, dielectrophoresis can also be caused in which the molecule M can be guided "regardless of the polarity of the molecule." Hence, a dielectrophoretic force can be used to carry out switching without concern for the polarity of the molecule, and can thus be used for various purposes.

That is, if the sample contains molecules of a first type and molecules of a second type, the use of the channel device according to the present invention allows the molecules to be separated from the sample one by one. Since the molecules are separated one by one, the separation can in principle be achieved at a purity of 100%. Guiding the molecule through different branching channels to different outlets (in other words, a switching operation of switching the branching channel) involves two operation modes, that is, a mode with switching and a mode with no switching.

(1) Mode with Switching

This mode is classified into a submode 1 in which the electric stimulus is changed by switching and a submode 2 in which the electrode pair is selected by switching.

In the submode 1, with the molecule M flowing from left to right in FIG. 1B, the type of the molecule is pre-sensed, and a DC voltage specific to the molecule A or an AC voltage with a frequency A specific to the molecule A is applied to between the paired electrodes (E1 and E2) to guide the molecule A to the branching channel 12a. When the type of another molecule B is sensed, a DC voltage specific to the molecule B or an AC voltage B with a frequency specific to the molecule B is applied to between the paired electrodes (E1 and E2) to guide the molecule B to the branching channel 12b. In this case, a plurality of DC voltages specific to the molecule A or B or a plurality of AC voltages with a frequency specific to the molecule A or B may be applied.

In the submode 2, with the molecule M flowing from left to right in FIG. 1B, the type of the molecule is pre-sensed, and the electrode pair (electrodes E1 and E3) corresponding to the molecule A is selected. A predetermined DC voltage or an AC voltage A with a predetermined frequency is applied to between the electrodes to guide the molecule A to the branching channel 12a. When another molecule B is sensed, the electrode pair (electrodes E2 and E4) corresponding to the molecule B is selected. A predetermined DC voltage or an AC voltage B with a predetermined frequency is applied to between the electrodes to guide the molecule B to the branching channel 12b. In this case, the DC voltage or the AC voltage A with the predetermined frequency may be the same as or different from the DC voltage or the AC voltage B with the predetermined frequency.

(2) Mode with No Switching

With no molecule pre-sensed, a DC voltage specific to the molecule A or an AC voltage with a frequency specific to the molecule A is applied to between the paired electrodes (E1 and E2) or between the paired electrodes (E1 and E3) or between the paired electrodes (E2 and E4). The voltage is applied for all molecules passing through the channel. This allows only the molecule A to be guided to a predetermined branching channel.

The (1) mode is desirable for exhaustively and individually separating and recovering all the molecules, and the (2) mode may also be used to take only targeted molecules out.

The manner of branching from the nanochannel via the branching portion to the plurality of branching channels is not limited to the Y-shaped branching shown in FIG. 1B. For example, a shape shown in FIG. 1C or 1D may be used. Furthermore, there is no upper limit on the number of branching channels.

The channel device according to the present invention is not limited to the identification or separation of molecules but may be used for different purposes. For example, a connected body of the molecules A and B may be synthesized by allowing the molecules A and B to flow through the nanochannel in order, and electrically stimulating the molecules A and B via the electrode pair to allow the molecules A and B to react with each other as a result of an electrochemical reaction or an increase in ambient temperature. Alternatively, a plurality of input sections (a cross section of the input section may have a nanometer size or a micrometer size) may be provided at the inlet side of the nanochannel, and there is no upper limit on the number of input sections.

The present invention also provides a sample treatment apparatus including a channel device with a nanochannel through which single molecule flows and a least one electrode pair arranged near the nanochannel (FIG. 1A), an AC power source that applies an AC voltage to the electrodes (FIG. 1B), and a measurement section that identifies single molecule contained in a sample flowing through the channel (FIG. 1B) (a fourth basic invention).

The present invention also provides a sample treatment apparatus including a channel device with a nanochannel through which single molecule flows, a branching portion, a plurality of branching channels, and i) at least one electrode pair arranged near the nanochannel in such a manner that the nanochannel is located between electrodes or ii) an electrode pair with one of the electrodes located near the nanochannel and the other located near the branching channels (FIG. 1A), and a switching section electrically stimulating, via the electrode pair, single molecule contained in a sample flowing through the nanochannel to urge the molecule to perform dynamic behavior in such a manner that the dynamic behavior allows the molecule to be guided to a predetermined one of the branching channels (FIG. 1B) (a fifth basic invention).

Now, an applied invention with the electrical nature embodied therein, an applied invention with the electric stimulus embodied therein, and an applied invention with the dynamic behavior embodied therein will be described, all of which belong to the present invention.

A sample treatment apparatus according to the present invention includes a channel device, a measurement section, and an arithmetic processing section. The channel device includes an injection section from which a sample to be treated is injected, and a nanochannel having a cross section of a nanometer order size and through which a molecule contained in the sample is allowed to migrate. The measurement section applies a voltage to between paired electrodes installed in the nanochannel and measures a resistance value or impedance when the molecule passes between the paired electrodes. Furthermore, the arithmetic processing section identifies the molecule based on the resistance value or impedance value measured by the measurement section.

The sample treatment apparatus further includes a plurality of output sections from which the molecule having migrated through the nanochannel is taken out and a molecule separation section that separates the identified molecule from the sample. In this case, the measurement section is arranged in the nanochannel to measure the resistance value or the impedance value, and the nanochannel is connected, via a branching portion, to a plurality of branching channels and to the output sections located beyond the branching channels. The molecule separation section guides the identified molecule from the nanochannel to the desired one of the plurality of branching channels.

A sample treatment apparatus according to the present invention separates molecules contained in a sample according to type, and includes a channel device, a measurement section, an arithmetic processing section, and a molecule separation section. The channel device includes an injection section from which a sample is injected, a nanochannel having a cross section of a nanometer order size and through which a molecule contained in the sample is allowed to migrate, and a plurality of output sections from which the molecule having migrated through the nanochannel is taken out. The nanochannel is connected, via a branching portion, to a plurality of branching channels and to the output sections located beyond the branching channels. The measurement section applies a voltage to between paired electrodes installed in the nanochannel and measures a resistance or impedance when the molecule migrates (traverses) between the paired electrodes. Furthermore, the arithmetic processing section associates the molecule with the resistance value or impedance value measured by the measurement section. The molecule separation section guides the molecule associated with the measured resistance value or impedance value from the nanochannel to a desired one of the plurality of branching channels.

In the above-described sample treatment apparatus, a plurality of electrode pairs may be provided in the nanochannel and arranged at predetermined intervals. In this case, the measurement section measures the resistance or impedance when the molecule passes through the electrode pair. Furthermore, the arithmetic processing section calculates a migration speed of the molecule based on a difference in the time when the resistance value or the impedance value is measured, and controls a timing for applying a voltage (electric field) based on the calculated migration speed of the molecule.

Moreover, in the above-described apparatus, the molecule separation section includes a predetermined electrode formed of an electrode pair provided on a nanochannel side or a common electrode, a plurality of outlet electrodes provided at the respective plurality of branching channels, a voltage application section that applies a voltage to between the predetermined electrodes or between the predetermined electrode and the outlet electrode, and a switching section that selects i) the predetermined electrode formed of the electrode pair or ii) a pair of the predetermined electrode and one outlet electrode or iii) a pair of the predetermined electrode and another outlet electrode or iv) a pair of the predetermined electrode and another outlet electrode or v) a pair of the predetermined electrode and so on. The arithmetic processing section determines one of the pairs i), ii), iii), iv), and v) based on information on the identified molecule, and controls the molecule separation section so that a DC voltage or an AC voltage is applied to the determined pair.

In the above-described apparatus, the channel device is formed of a hydrophilic insulator material. In this case, the sample is introduced from the injection section into the nanochannel by capillary action. Alternatively, one of the paired guiding electrodes that apply a DC voltage or an AC voltage to the sample may be arranged in the injection section, and the other may be arranged in the nanochannel. In this case, an electric field is generated between the paired guiding electrodes to guide the sample from the injection section into the nanochannel.

Furthermore, to accomplish the object, the sample treatment apparatus according to the present invention includes a channel device, a DC power source or an AC power source, a measurement section, and an arithmetic processing section. The channel device includes an injection section from which a sample to be treated is injected, and a nanochannel having a cross section of a nanometer order size and through which a molecule contained in the sample is allowed to migrate. When a molecule is present between electrodes of an electrode pair installed in the nanochannel, the measurement section applies a DC voltage or an AC voltage to between the electrodes and measures resistance or impedance obtained. Furthermore, the arithmetic processing section identifies the molecule based on the resistance value or impedance value measured by the measurement section. The injection section preferably has a cross-sectional size ranging from nanometer order to micrometer order.

The sample treatment apparatus further includes a plurality of output sections having a cross-sectional size ranging from nanometer order to micrometer order and from which the molecule having migrated through the nanochannel is taken out and a molecule separation section that separates the identified molecule from the sample. In this case, the nanochannel is connected, via a branching portion, to a plurality of branching channels and to output sections located beyond the branching channels. The molecule separation section guides the identified molecule from the nanochannel to a desired one of the plurality of branching channels.

Furthermore, another sample treatment apparatus according to the present invention separates molecules contained in a sample according to type, and includes a channel device, a DC power source or an AC power source, a measurement section, an arithmetic processing section, and a molecule separation section. The channel device includes an injection section from which a sample is injected, a nanochannel having a cross section of a nanometer order size and through which a molecule contained in the sample is allowed to migrate, and a plurality of output sections from which the molecule having migrated through the nanochannel is taken out. The nanochannel is connected, via a branching portion, to a plurality of branching channels and to the output sections located beyond the branching channels. The measurement section applies a DC voltage or an AC voltage to between electrodes of an electrode pair installed in the nanochannel and measures resistance or impedance when a molecule is present between the electrodes. Furthermore, the arithmetic processing section associates the molecule with the resistance value or impedance value measured by the measurement section. The molecule separation section guides the molecule associated with the measured impedance value from the nanochannel to a desired one of the plurality of branching channels.

In the above-described sample treatment apparatus, a plurality of electrode pairs may be provided in the nanochannel and arranged at predetermined intervals. In this case, the measurement section measures the resistance or impedance when the molecule passes between the paired electrodes. Furthermore, the arithmetic processing section calculates a migration speed of the molecule based on a difference in the time when the impedance value is measured, and controls a timing for applying a voltage (electric field) based on the calculated migration speed of the molecule.

Moreover, in the above-described apparatus, the molecule separation section includes a predetermined electrode formed of an electrode pair provided on a nanochannel side or a common electrode, a plurality of outlet electrodes provided at the respective plurality of branching channels, a voltage application section that applies a voltage to between the predetermined electrodes or between the predetermined electrode and the outlet electrode, and a switching section that selects i) the predetermined electrode formed of the electrode pair or ii) a pair of the predetermined electrode and one outlet electrode or iii) a pair of the predetermined electrode and another outlet electrode or iv) a pair of the predetermined electrode and another outlet electrode or v) a pair of the predetermined electrode and so on. The arithmetic processing section determines one of the pairs i), ii), iii), iv), v) . . . based on information on the identified molecule, and controls the molecule separation section so that a voltage is applied to the determined pair.

In the above-described apparatus, the channel device is formed of a hydrophilic insulator material. In this case, the sample is introduced from the injection section into the nanochannel by capillary action. Alternatively, one of the paired guiding electrodes that apply an electric field to the sample may be arranged at the injection section, and the other may be arranged in the nanochannel. In this case, an electric field is generated between the paired guiding electrodes to guide the sample from the injection section into the nanochannel.

Moreover, in the sample treatment apparatus according to the present invention, the AC power source applies an AC voltage to between the electrodes of the electrode pair installed in the nanochannel with at least a frequency of the AC voltage varied.

On the other hand, the measurement section may retain the molecule between the paired electrodes to change an environment of the molecule and measure the impedance when the AC voltage is applied to between the electrodes with the frequency of the AC power source varied. The arithmetic processing section senses the conformation of the molecule and the dynamic state thereof based on the impedance value measured by the measurement section. Furthermore, the voltage to be applied by the AC power source to between the paired electrodes in the nanochannel is variable in value. In this case, the measurement section measures the impedance with the frequency and voltage value of the AC power source varied. The arithmetic processing section senses the conformation of the molecule or dynamic changes therein (dynamic state) based on changes in impedance value occurring when the frequency and voltage value of the AC power source are changed.

Further features of the present invention will be clear from embodiments for carrying out the invention and attached drawings.

Advantageous Effects of the Invention

The present invention can in principle achieve an identification or separation accuracy of 100%. The present invention can identify or separate the desired molecules even from a small amount of sample in a short time compared to the conventional technique. This enables a reduction in apparatus size.

Furthermore, the present invention can identify or separate molecules that are the same in molecular size but different in type, allowing the conformation of biomolecules or dynamic changes therein (dynamic state) to be sensed.

BRIEF DESCRIPTION OF DRAWINGS

FIG. 1E is a diagram showing an example of a general configuration (5) in which the channel device according to an embodiment of the present invention is viewed from above.

FIG. 11 is a diagram showing results of experiments in which a mixture of three DNA solutions is used and in which the DNA molecules are simultaneously separated from the mixture.

FIG. 16 is a diagram showing the results of experiments in which a frequency of an AC power source is varied and in which a voltage is swept at each frequency.

FIG. 20 is a diagram showing a different electrode pattern formed on a substrate and an electric field obtained.

FIG. 21 is a diagram illustrating steps of forming an electrode pattern.

FIG. 22 is a diagram showing how an insulating film is coated on the electrode pattern.

FIG. 23 is a diagram illustrating features of the rectangular channel and the V-shaped channel by comparison.

FIG. 24 is a diagram (electron microscope photograph) showing an actually produced channel device.

DESCRIPTION OF EMBODIMENTS

Figure 1A:
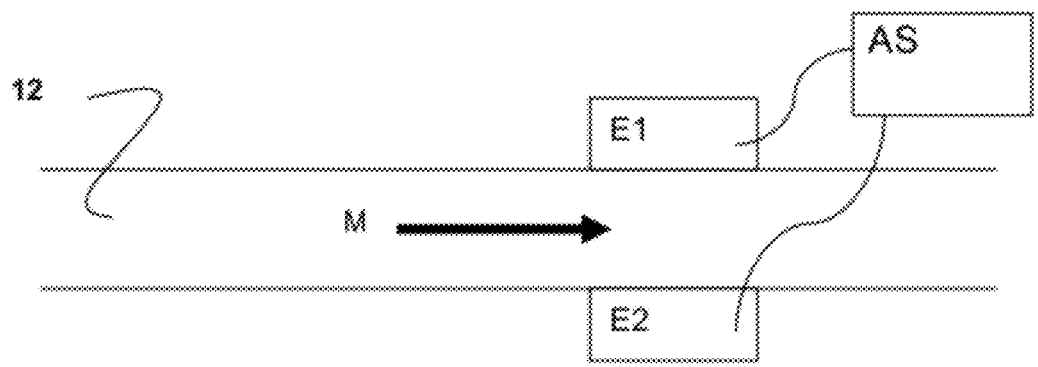
FIG. 1A is a diagram showing an example of a general configuration (1) in which a channel device according to an embodiment of the present invention is viewed from above.
Figure 1B:
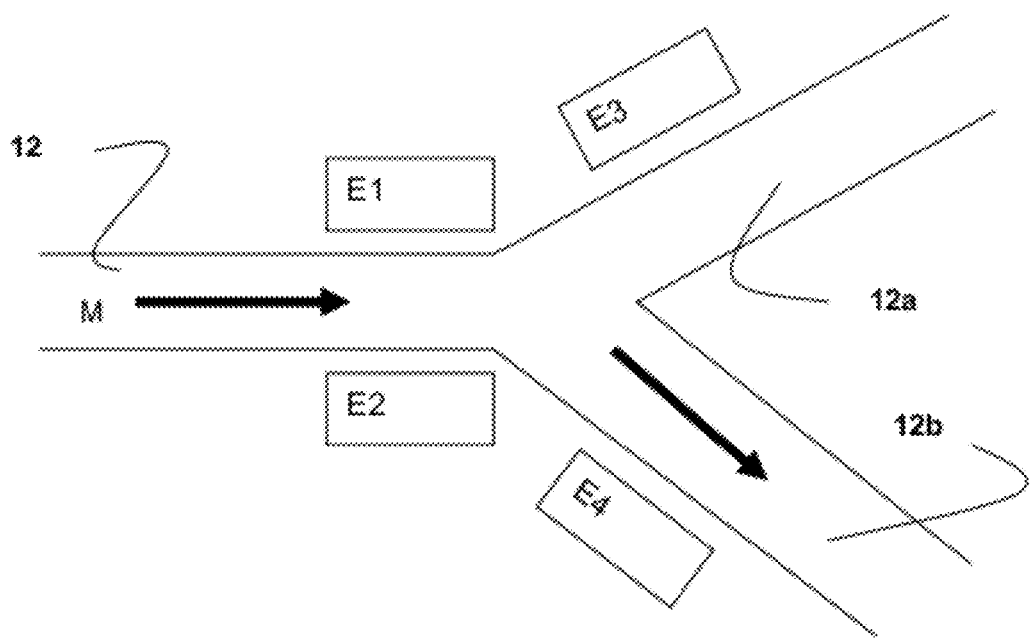
FIG. 1B is a diagram showing an example of a general configuration (2) in which the channel device according to an embodiment of the present invention is viewed from above.
Figure 1C:
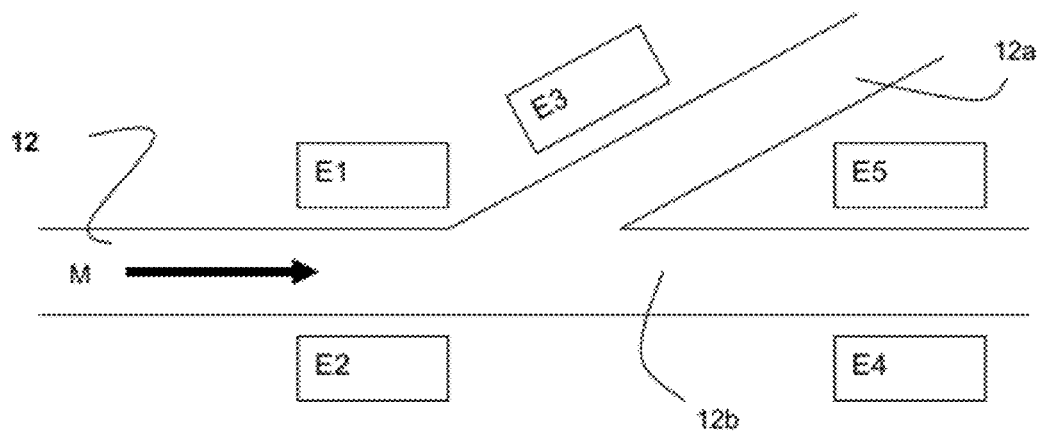
FIG. 1C is a diagram showing an example of a general configuration (3) in which the channel device according to an embodiment of the present invention is viewed from above.
Figure 1D:
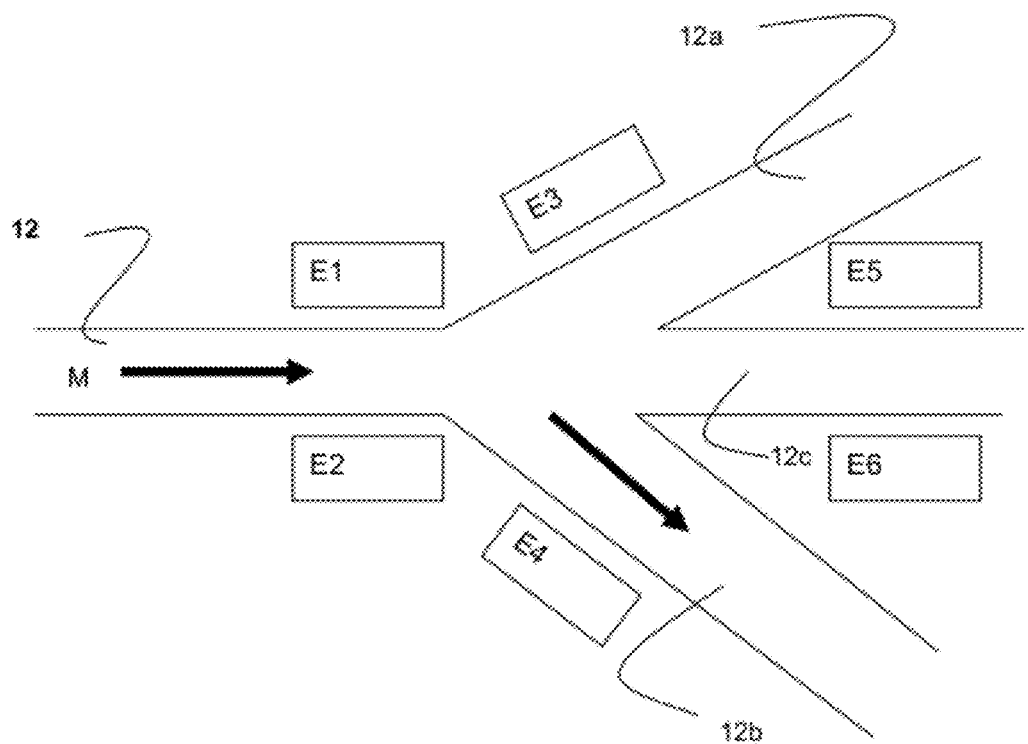
FIG. 1D is a diagram showing an example of a general configuration (4) in which the channel device according to an embodiment of the present invention is viewed from above.

The present invention provides a molecule separation apparatus (an example of a sample treatment apparatus) which can achieve identification and separation of molecules (even molecules that are the same in size but different in type) at an accuracy of 100% in principle under ideal conditions (the conventional method cannot separate the molecules from one another at an accuracy of 100% even under ideal conditions), which can sense the conformation of the molecule and dynamic changes therein (dynamic state), and which can be reduced in size.

A sample to be treated according to the present invention may be water-soluble molecules dissolved or suspended in a hydrophilic solvent or may be generated by dissolving or suspending hydrophobic molecules in a hydrophobic solvent (for example, acetone, ethyl acetate, methyl acetate, or toluene). The solvent is a carrier medium allowing a molecule to migrate through a nanochannel.

Embodiments of the present invention will be described below with reference to the attached drawings. However, the embodiments are only examples for implementing the present invention and are not intended to limit the technical scope of the present invention. Furthermore, components common to different figures are denoted by the same reference numerals.

I. First Embodiment

A first embodiment relates to a molecule separation apparatus (sample treatment apparatus) which applies a voltage between electrodes of an electrode pair installed at a nanochannel and which measures a resistance based on a current flowing when a molecule is present between the electrodes to identify the molecule based on the measured resistance value.

<Configuration of Channel Device in Molecule Separation Apparatus>

FIG. 1E is a diagram showing an external configuration of a channel device 10 using a molecule separation apparatus (sample treatment apparatus) according to the embodiment of the present invention. The channel device 10 includes an injection section 11 from which a sample is injected, a nanochannel 12 that is a section in which processing of identifying and separating a molecule is carried out, and output sections 13 and 14 from which the separated molecule is taken out; the injection section 11, the nanochannel 12, and the output sections 13 and 14 are all formed on a substrate.

The substrate may be formed of an insulating material such as quartz, glass, plastic, or ceramic. If the hydrophilicity of the substrate is utilized to treat the sample (for example, capillary action is utilized to introduce the sample into the nanochannel 12), it is important to form the substrate of quartz or glass. The nanochannel 12 is excessively thin, and feeing the sample into and out of the nanochannel 12 is difficult. Thus, a channel with a larger size may be utilized as an interface to the nanochannel. In this case, the injection section 11 and the output sections 13 and 14 need not be nanochannels but may be channels larger in size. For the injection section 11 and the output sections 13 and 14, for example, an inlet and an outlet are 1 to 3 mm in diameter and a channel is 1 to 100 μm in width and 1 to 10 μm in depth. Moreover, the nanochannel 12 is, for example, several nm to 500 nm in both width and depth. The length of each channel is not particularly limited and may be determined in view of apparatus size.

Figure 2:
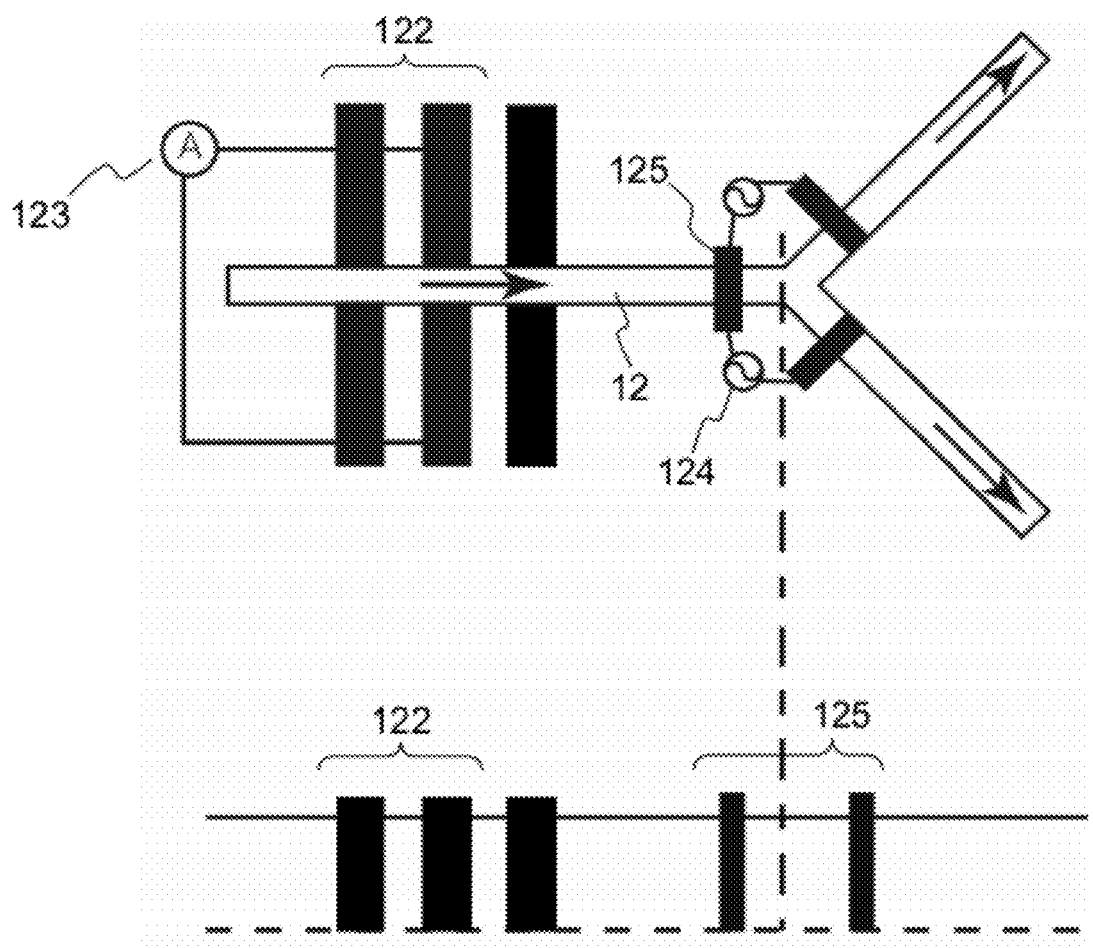
FIG. 2 is a diagram showing a detailed configuration of the channel device according to a first embodiment (FIG. 1E) as viewed from above a nanochannel.

FIG. 2 is a diagram showing a more detailed configuration of the nanochannel 12. As shown in FIG. 2, the nanochannel 12 is formed of the nanochannel 12 to which a plurality of branching channels are coupled, measuring nanoelectrodes 122 that identify a molecule passing through the nanochannel, a measuring ammeter 123 that measures a resistance based on a current flowing through a passing sample, and switching nanoelectrodes 125 installed at a branching portion of the nanochannel to guide the molecule to a desired channel. A checking ammeter 124 may be installed in the nanochannel to measure the resistance based on a current flowing through the sample during switching to check whether the molecule has been introduced into its original channel.

The measuring nanoelectrodes 122 are preferably formed of a plurality of pairs of electrodes. When a plurality of pairs are provided, a time required for a molecule with its resistance measured by the first electrode pair to reach a downstream electrode pair is measured to enable the flow velocity of the molecule flowing through the nanochannel to be sensed. Then, based on the flow velocity, a time required for the molecule to reach the switching nanoelectrodes 125 can be calculated. Thus, the molecules can be appropriately separated into the respective desired channels. The switching nanoelectrodes 125, installed in the branching portion of the nanochannel 12, include a common electrode and outlet electrodes provided at respective outlet channels. Each molecule can be guided to the desired branching channel (switch on) by applying a predetermined voltage (in terms of electric field, an electric field of about several MHz and several MV/m) to between each outlet electrode and the common electrode.

Figure 3:
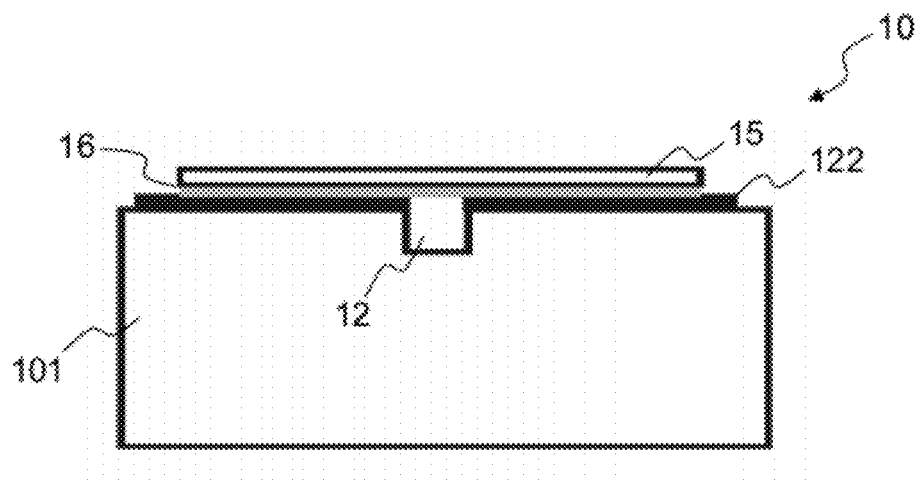
FIG. 3 is a cross-sectional view of the channel device shown in FIG. 1E, the view being taken along a line AA' in FIG. 1E.

FIG. 3 is a cross-sectional view of the channel device 10 (FIG. 1E) taken along a line AA' (corresponding to a portion of the channel device 10 in which the measuring nanoelectrode is provided). In the channel device 10, the nanochannel 12 (which is actually shallower than the electrodes) is formed on a substrate 101, and the measuring nanoelectrodes 122 and the switching nanoelectrodes 125 are arranged on the nanochannel 12. Then, a glass plate 15 and the substrate 101 are bonded together using an adhesive member 16. For example, the adhesive member 16 may be PDMS (Polidimethylsiloxane) doped with $SiO_2$. This allows the glass plate to be bonded to the substrate while covering the electrodes thicker than the nanochannel 12.

<Circuit Configuration of Molecule Separation Apparatus>

Figure 4:
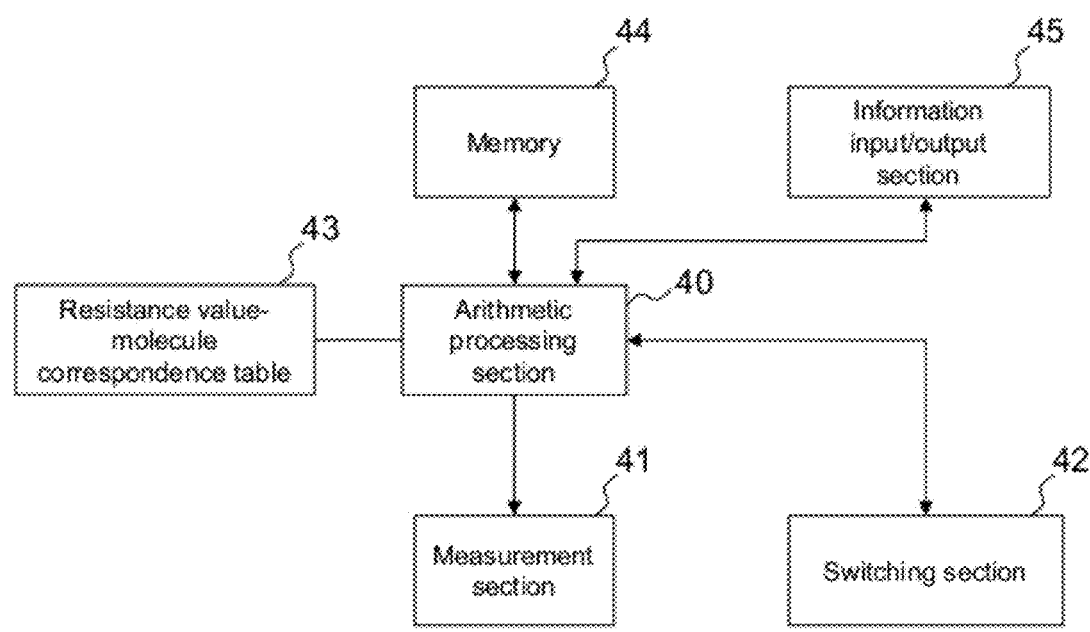
FIG. 4 is a block diagram showing a circuit configuration of a molecule separation apparatus according to the first embodiment of the present invention.

FIG. 4 is a block diagram showing a circuit configuration of the molecule separation apparatus according to the first embodiment of the present invention. The molecule separation apparatus includes an arithmetic processing section 40 that acquires information from components of the apparatus to carry out predetermined calculations in order to control the components as necessary, a measurement section 41 with the measuring nanoelectrodes 122, the measuring ammeter 123, and a power source (not shown in the drawings) which applies a voltage to the electrode 122, a switching section 42 with the switching nanoelectrodes 125, the checking ammeter 124, and a voltage application section (not shown in the drawings) which applies a voltage to between each of the electrodes and the common electrode, a resistance value-molecule correspondence table 43 showing the correspondence relationship between each of various molecules and resistance values obtained when a voltage is applied to a sample with the various molecules, a memory 44, and an information input/output section 45 to which a user inputs predetermined instructions and the like and which outputs (displays) the results of a separation treatment.

The arithmetic processing section 40 acquires, from the measurement section 41, a resistance value obtained when a molecule passes through the nanochannel 12, and checks the resistance value against the resistance value-molecule correspondence table 43 to identify the type of the passing molecule (the measured resistance value is temporarily stored in the memory 44). If a molecule contained in the sample is unknown, the corresponding measured resistance value is absent from the table 43. Thus, the measured resistance value is stored in the memory 44, and the molecule is separated from the sample with the type of the molecule remaining unknown. However, it should be noted in the description below that the ammeter measures a current value and thus in order to measure the resistance value, the measurement section 41 and the switching section 42 need to calculate the resistance value from the applied voltage and the current value.

Furthermore, the arithmetic processing section 40 measures the points of time at which a molecule passes between electrodes of each of a plurality of electrode pairs of the measuring nanoelectrodes 122 included in the measurement section 41, and calculates the flow velocity of the molecule from the measured point of time and the distances between the electrodes of the electrode pairs. Then, based on the distance from the final electrode pair of the measuring nanoelectrodes 122 to the switching nanoelectrodes 125 and the calculated flow velocity, the arithmetic processing section 40 gives the switching section 42 instructions regarding which of the outlet electrodes of the switching nanoelectrodes 122 is to be subjected to a voltage (electric field) applied to between the outlet electrode and the common electrode and at which timing the voltage is to be applied. In accordance with the instructions, the molecule is drawn into the desired branching channel in the switching section 42, and can thus be separated from the sample.

In the switching section 42, the checking ammeter 124 measures the resistance when the molecule passes by the checking ammeter 124 and supplies the measured value to the arithmetic processing section 40. Then, the arithmetic processing section 40 may compare the resistance value with that measured by the measurement section 41 to check whether the type of the molecule to be separated is correct.

<Operation of Molecule Separation Apparatus>

(1) Sample Injection and Flow Control

First, a sample is introduced into the injection section 11. The sample contains known and unknown molecules. The sample separation apparatus can classify the molecules according to type if the sample contains only known molecules, and if the sample contains unknown molecules, can classify these molecules as a group exhibiting the same resistance (impedance) value with the type of the molecules remaining unknown.

In the channel device 10, since the substrate 101 is formed of quartz, glass, or the like, a wall surface of the channel is hydrophilic. Thus, the sample is automatically sucked through the injection section 11 and then through the nanochannel 12 and finally into the output sections 13 and 14 (outlet side) by capillary action. Then, only a very small amount of liquid flows out of the outlet portion, and thus all of an instantaneously outflowing carrier medium evaporates. Hence, in order to compensate for the liquid lost by evaporation, the sample voluntarily continues to flow by capillary action, leading to a given amount of flow in the nanochannel 12. Furthermore, since only the carrier medium evaporates, the molecule is concentrated before being separated and recovered. This is convenient for analysis of the molecule during a post-process. This is also an important advantage. Even if the molecule is successfully recovered, when the concentration of the molecule is low, the molecule cannot be analyzed because of the low sensitivity of conventional assays.

Furthermore, the flow velocity can be controlled to some degree by cooling the whole or a part of the channel device 10. For example, at a temperature close to the room temperature, all of the sample having left the nanochannel 12 evaporates upon approaching the output sections 13 and 14. Hence, when the whole or a part of the channel device 10 is cooled in order to prevent the evaporation, the sample flows to the outlet. The temperature for cooling may be between about 4° C. and about 25° C. (room temperature).

Here, the capillary action is utilized to introduce the sample into the nanochannel 12. However, the present invention is not limited to this. As described below (variation), the sample can be electrically controlled so as to be introduced into the nanochannel.

(2) Sensing of Single Molecule

Since the width of the nanochannel 12 is of the order of nanometers, each molecule contained in the sample migrates through the nanochannel 12 in the form of a single molecule.

In the molecule separation apparatus according to the first embodiment of the present invention, the measurement section 41 uses the ammeter 123 to measure the resistance value based on a current flowing between the paired electrodes of the measuring nanoelectrodes 122. When the molecule passes through the measuring nanoelectrodes 122, the resistance changes. Furthermore, the resistance varies depending on the type of the molecule (for example, molecular size). This nature can be utilized to identify the molecule.

The arithmetic processing section 40 acquires the measured resistance value from the measurement section 41 and stores the acquired resistance value in the memory 44. The arithmetic processing section 40 further checks the acquired resistance value against the resistance value-molecule correspondence table 43. The arithmetic processing section 40 identifies the molecule and continues the separation treatment if the table 43 contains the molecule corresponding to the acquired resistance value. The arithmetic processing section 40 continues the separation treatment without identifying the molecule if the table 43 does not contain the molecule corresponding to the acquired resistance value.

If the measuring nanoelectrodes 122 are formed of a plurality of electrode pairs, the arithmetic processing section 40 calculates the migration speed (flow velocity) in (the electrode arrangement area of) the nanochannel 12 based on the time delay of the resistance value at each electrode pair, and further carries out a calculation to determine what seconds later the molecule reaches the branching portion of the nanochannel 12. This allows the migration speed of a particular molecule to be sequentially calculated. Thus, even for a molecule the migration speed of which is unknown, the separation treatment can be appropriately carried out. In the present embodiment, the measuring nanoelectrodes 122 are formed of a plurality of electrode pairs. However, for a molecule the migration speed of which is known, a plurality of electrode pairs need not be provided but installing a single electrode pair suffices.

(3) Switching

As described above, the timing when the molecule to be separated reaches the branching portion of the nanochannel 12 can be determined. Thus, at this timing, the arithmetic processing section 40 applies an electric field to between the common electrode of the switching nanoelectrodes 125 and the outlet electrode on the channel side to which the target molecule is to be guided, depending on the type of the molecule or the current value thereof. Then, one of dielectrophoresis, electrophoresis, and an electroosmotic flow acts in the direction of the branching channel to which the molecule is to be guided from the nanochannel, thus allowing the molecule to be guided to the branching channel.

In the present embodiment, the example is illustrated in which the channel device 10 includes the nanochannel and the two branching channels branching from the nanochannel. However, the present invention is not limited to this. Of course, the number of the branching channels may be equal to the number of the types of the molecules to be separated. Furthermore, a method for providing a plurality of branches (branching channels) branching from the nanochannel may be to provide a plurality of branching channels simultaneously branching from a single nanochannel or to cascade bifurcated arrangements together to finally form a plurality of branches. The configuration of the branching channels is not limited.

<Variation>

(1) Sample Introduction (i) In the above-described embodiment, capillary action is utilized to introduce the sample from the microchannel to the nanochannel. Now, means for electrically controlling the sample so that the sample is introduced into the nanochannel will be described. When the sample is thus introduced based on the electric control, accurate flow control can be achieved to improve measurement accuracy and separation accuracy. Furthermore, the substrate 101 of the channel device 10 need not be hydrophilic and can thus be formed even of a material such as plastic or ceramic.

Figure 5:
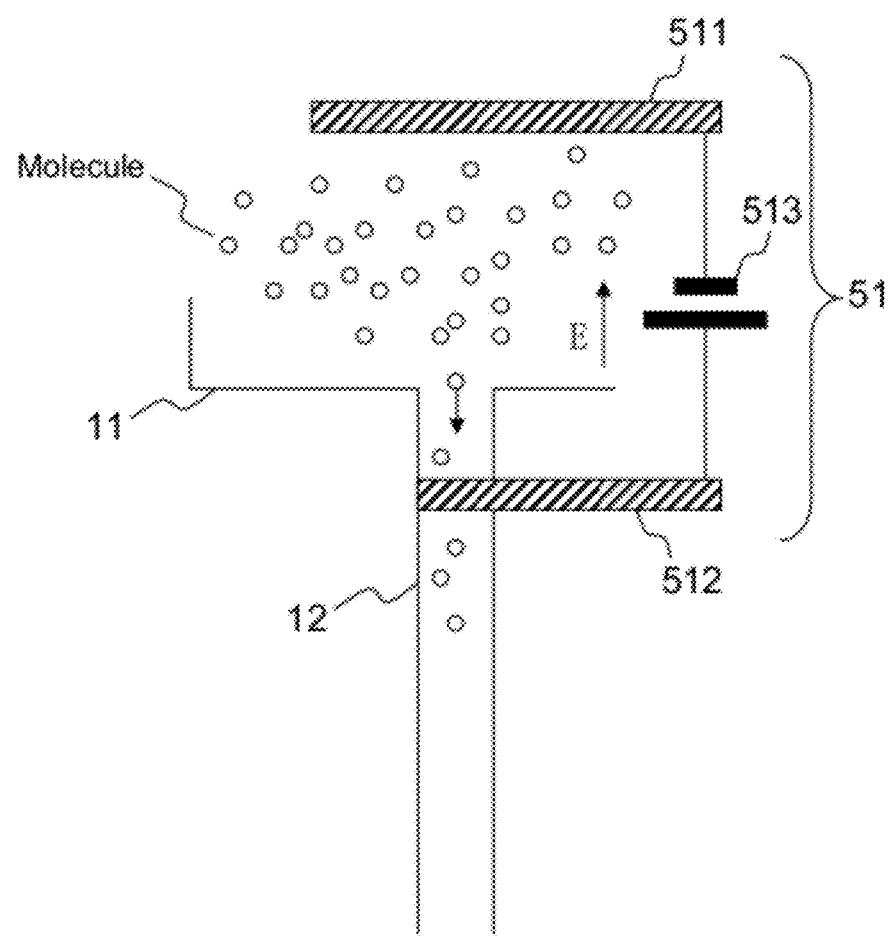
FIG. 5 is a diagram showing a general configuration of a sample introduction section for use in a variation of the first embodiment and a second embodiment of the present invention.

FIG. 5 is a diagram showing a configuration of a sample introduction section 51 according to a variation. The sample introduction section 51 includes paired electrodes 511 and 512 that apply an electric field to a sample, and a power source 513. In this case, the electrode 511 is provided on the side of the injection section 11, and the electrode 512 is provided on the side of the nanochannel 12.

Here, molecules are charged, and negatively charged molecules are drawn in the direction of the nanochannel 12 when an electric field is applied to the sample in a direction shown in FIG. 5. On the other hand, for positively charged molecules, an electric field may be applied in the opposite direction. In this manner, each molecule of the sample can be introduced into the nanochannel 12 by switching the direction in which an electric field is applied depending on whether the sample is positively or negatively charged.

Figure 6:
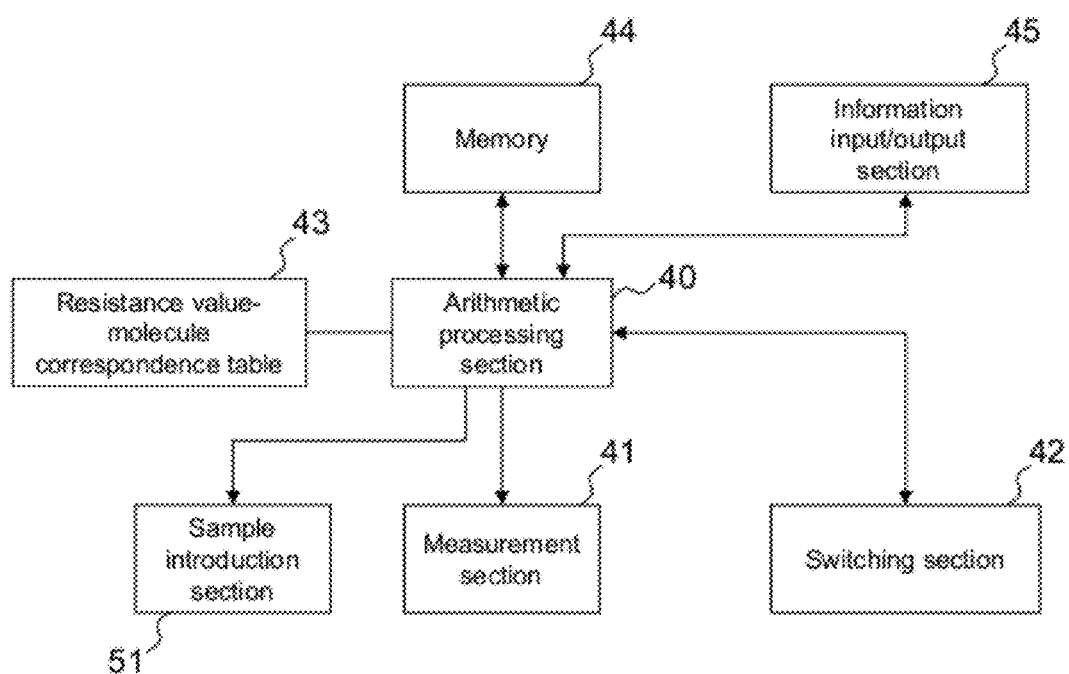
FIG. 6 is a block diagram showing a circuit configuration of a molecule separation apparatus according to a variation of the first embodiment of the present invention.

FIG. 6 is a block diagram showing a circuit configuration of a molecule separation apparatus according to the variation. FIG. 6 is the same as FIG. 4 except that the molecule separation apparatus in FIG. 6 includes the sample introduction section 51. A voltage applied to an electrode in the sample introduction section 51 (the direction of the application, the value of the voltage, and the like) is controlled by the arithmetic processing section 40 in accordance with an instruction input via the information input/output section 45.

(ii) Furthermore, the sample may be introduced utilizing an electroosmotic flow. In this case, a hydrophilic material such as glass is preferably used for the substrate 101 of the channel device 10. Glass is negatively charged, and thus positive ions in the sample are drawn to the negative charges in the glass to form an electrical double layer. When a voltage is applied to the electrical double layer, the charged portion of the sample migrates and the whole sample correspondingly starts to flow. This is the principle of sample introduction using an electroosmotic flow. The surface of the electroosmotic flow may be positively or negatively charged.

(2) Configuration of Nanochannel (Molecule Measurement Area)

Figure 7:
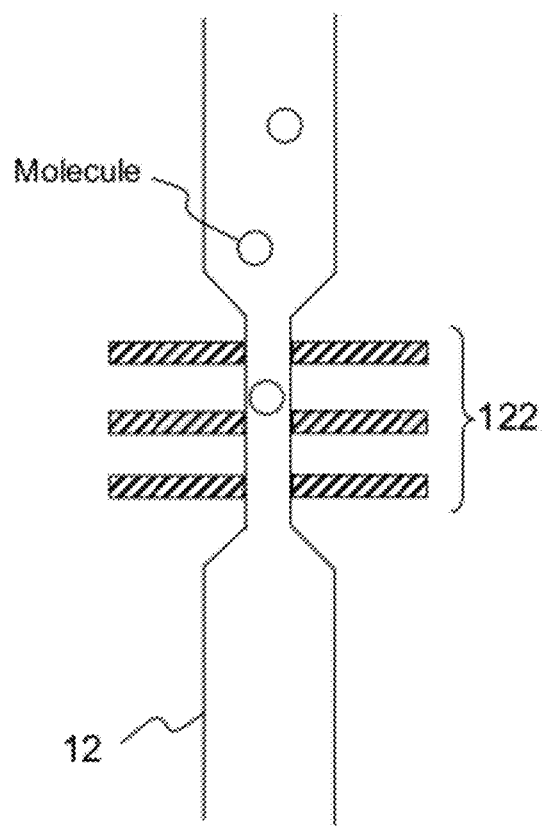
FIG. 7 is a diagram showing a configuration of a nanochannel according to the variation of the first and second embodiments of the present invention.

FIG. 7 is a diagram showing another example of configuration of an area of the nanochannel 12 in the channel device 10 in which the measuring nanoelectrodes 122 are arranged. As described above, the measuring nanoelectrodes 122 are used to sense a molecule flowing through the nanochannel and to calculate the migration speed of the molecule based on a difference in the timing of current value measurement among the plurality of electrode pairs. In this example, to allow the molecule to be more appropriately identified, the width of the resistance measurement area of the nanochannel is set smaller than that of the remaining area. This makes a change in current caused by the molecule proportional to the volumetric ratio of the volume of the molecule to the volume between the electrodes. Thus, the volumetric ratio increases with decreasing volume between the electrodes. This increases the magnitude of a change in current caused by the molecule, allowing the resistance to be sensitively measured.

<Experiments>

Experiments conducted based on the principle and operation described in the first embodiment will be described to demonstrate the effectiveness of the present invention.

(1) Specification of Nanochannel

Experiments were conducted using a nanochannel configured to have an overall length of 150 μm, an overall depth of 50 to 100 nm, and an overall width of 50 to 500 nm.

(2) Sample Used

Figure 8:
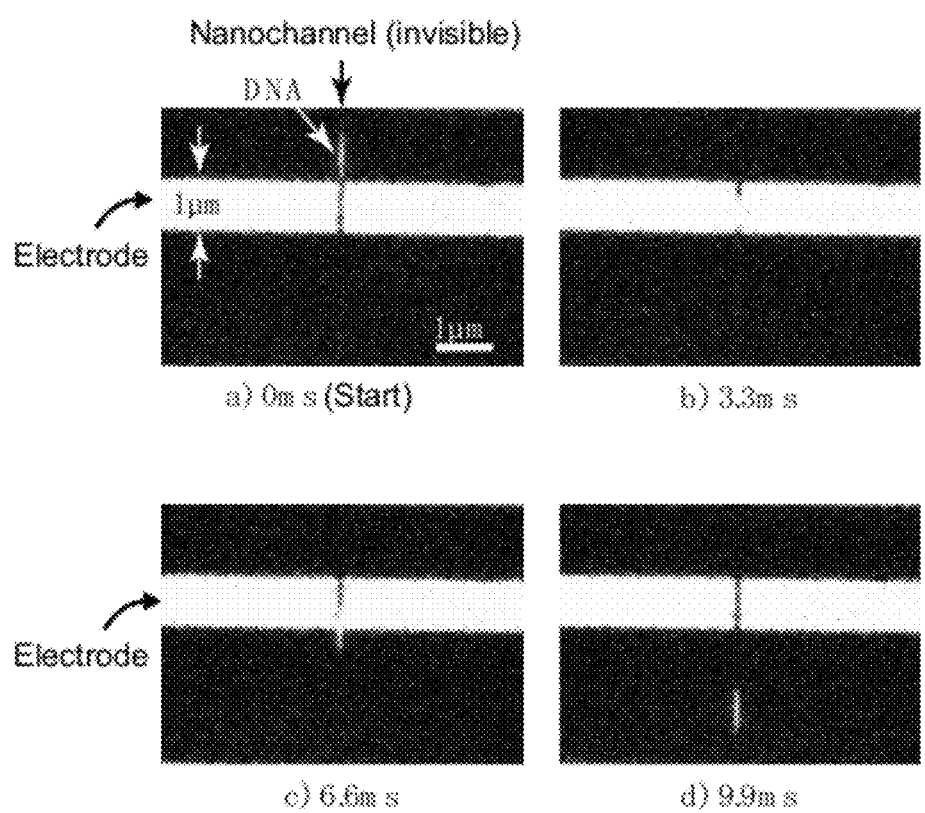
FIG. 8 is a diagram (photographs) showing a DNA of size 15.0 kbp migrating through a nanochannel; the photographs were taken at time intervals of 3.3 ms.

Three DNA solutions (samples) containing the respective types of DNAs of size 15.0 kbp (kilo base pairs), 33.5 kbp, and 48.5 kbp were prepared and used for experiments. The concentration of each sample was adjusted to 1 fM in a 0.1×TBE buffer. The calculated predicted value of apparent length of each DNA was 1.1 µm for the 15.0-kbp DNA, 2.4 µm for the 33.5-kbp DNA, and 3.6 µm for the 48.5-kbp DNA.
(3) Voltage Applied to Measuring Nanoelectrode
0.1 V
(4) Contents of Experiments
(i) Each sample was independently introduced into the nanochannel. Then, i) the flow velocity of the sample was measured, ii) single molecule of the DNA was identified, and iii) the molecule was guided to the appropriate output section of the channel associated with the DNA (for the results of the experiment, see FIGS. 8 to 10).
(ii) In the subsequent experiment, the samples were mixed together into a new sample, and whether each DNA was successfully separated from the new sample was experimentally determined (for the results of the experiment, see FIG. 11).
(5) Results of Experiments
(i) FIG. 8 is a diagram (photographs) showing the DNA molecule of size 15.0 kbp migrating through the nanochannel; the photographs were taken at time intervals of 3.3 ms. The nanochannel is very small compared to the width of the electrode (1 µm) and is invisible on the figure. A white vertical line represents the position of the DNA migrating through the nanochannel.

Figure 9:
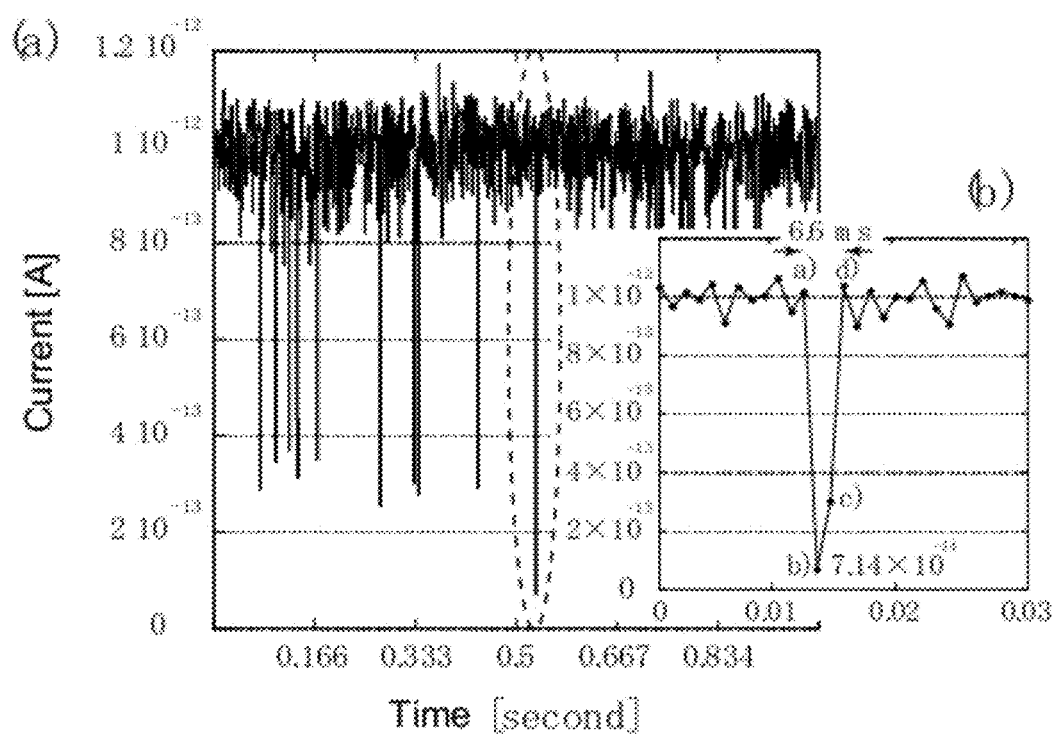
FIG. 9 is a graph showing a variation in a current value observed when the DNA of size 15.0 kbp migrates through the nanochannel.

FIG. 9 is a graph showing a variation in the current value obtained when the DNA molecule of size 15.0 kbp migrates through the nanochannel. FIG. 9(a) shows a variation in the current value obtained when the sample was allowed to flow continuously for a predetermined time. FIG. 9(b) is an enlarged view of a dotted portion of FIG. 9(a).

The current value changes sharply in a certain portion of FIG. 9(a) (the portion with a very small current value). In this portion, the DNA is passing through the electrode portion of the nanochannel and blocks the flow of a current to significantly change the current value. Thus, as shown in FIG. 9(b), in a state shown in FIG. 8(a), the DNA molecule is still far from the electrode portion, and the current value varies only by an amount corresponding to noise (the background current value was about 1 pA). In a state shown in FIG. 8(b), the DNA is passing through the electrode portion to completely block the current between the electrodes, and the very small current value is measured. As described above, the resistance value may be determined from the current value to identify the molecule or the molecule may be separated from the sample. Furthermore, as shown in FIGS. 8(c) and 8(d), the area in which the DNA and the electrode overlap decreases to recover the current value to the state shown in FIG. 8(a).

Figure 10:
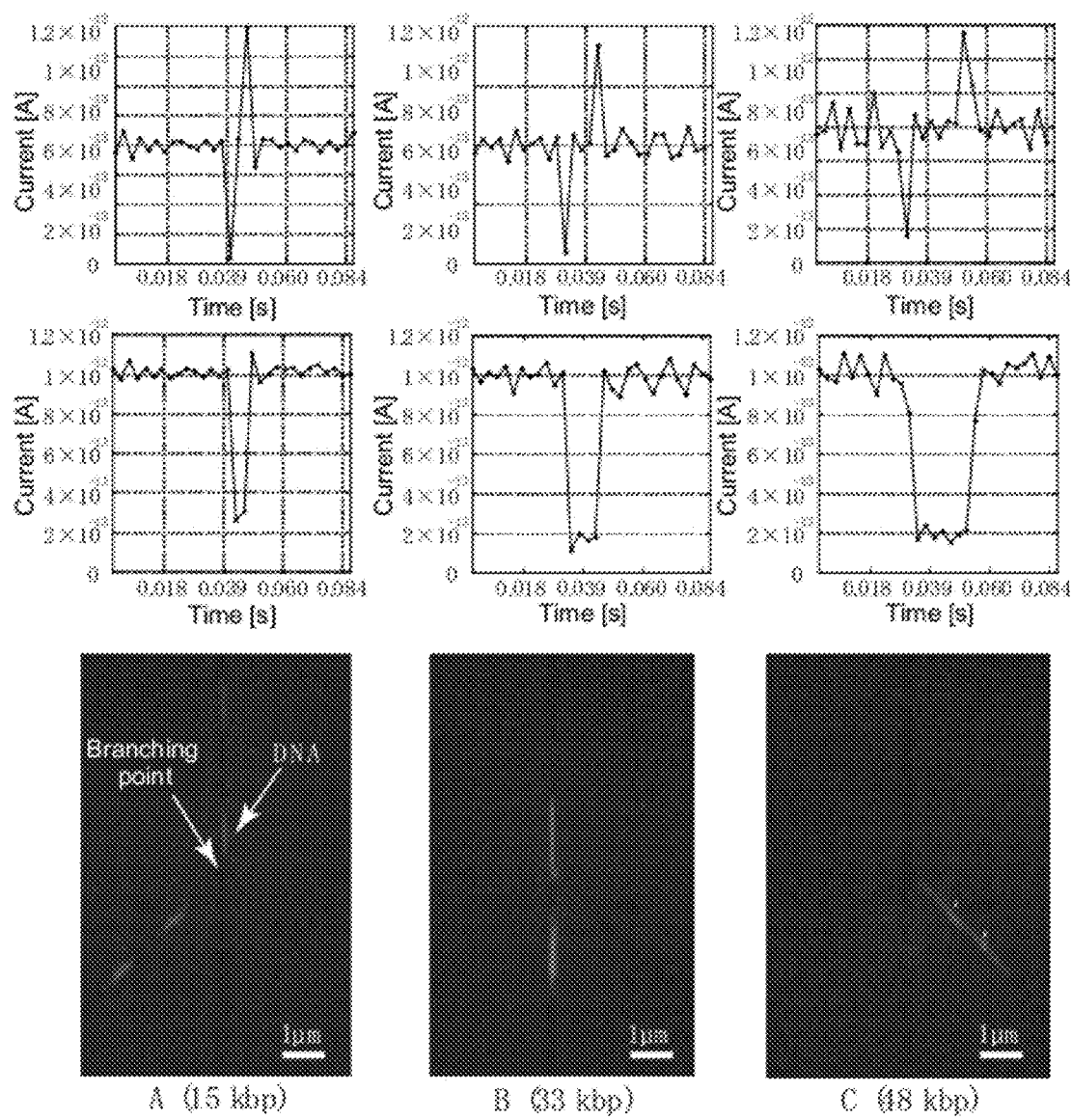
FIG. 10 is a diagram showing measured current values of DNA molecules of different sizes and also showing how each DNA molecule is separated from a sample.

FIG. 10 is a diagram showing the measured current values of the DNAs of the different sizes and also showing how each DNA is separated from the sample. Here, in a nanochannel with trifurcated branching channel, the DNA of size 15.0 kbp is guided to the left branching channel (see FIG. 10A). The DNA of size 33.5 kbp is guided to the central branching channel (see FIG. 10B). The DNA of size 48.5 kbp is guided to the right branching channel (see FIG. 10C).

As seen in the graphs in FIG. 10, when each DNA passes through the electrode portion, a change in current value which is specific to the DNA is exhibited. Then, the resistance value is determined based on the change in current value which is specific to the molecule, and a switching operation is performed at the branching portion of the nanochannel. Thus, the desired molecule can be guided to the desired branching channel.

(ii) In the subsequent experiment, the above-described three DNAs were mixed together in a solution, and the DNA molecules were simultaneously separated from the solution. FIG. 11 is a diagram showing results of experiments in which the DNA molecules were separated from the mixture. FIG. 11(A) shows the fluorescent emission intensities of the DNA molecules. FIG. 11(B) shows the fluorescent emission intensities of the DNA molecules before and after separation.

In the experiments, 6,000 molecules (the number of molecules contained in a 1-fM solution) were prepared for each DNA. However, the experiments were ended when only up to 100 molecules were counted; not all the molecules were counted due to time constraints or the like.

As also seen in FIG. 11(B), the fluorescent emission intensity of each DNA molecule before separation is almost equal to that after separation. Hence, the separation treatment was appropriately carried out using the molecule separation apparatus according to the present invention.

II. Second Embodiment

The second embodiment relates to a molecule separation apparatus which applies an AC voltage to between electrodes of an electrode pair installed in the nanochannel when a molecule is present between the electrodes and which measures the resulting impedance to identify the molecule based on the measured impedance value.

<Channel Device Configuration in Molecule Separation Apparatus>

The external configuration of the channel device 10 for use in the second embodiment and the configuration of the channel device as viewed in a cross section taken along a line AA' (corresponding to a portion of the channel device in which the measuring nanoelectrodes are provided) are the same as those in the first embodiment (see FIGS. 1E and 3) and the description thereof is omitted.

Figure 12:
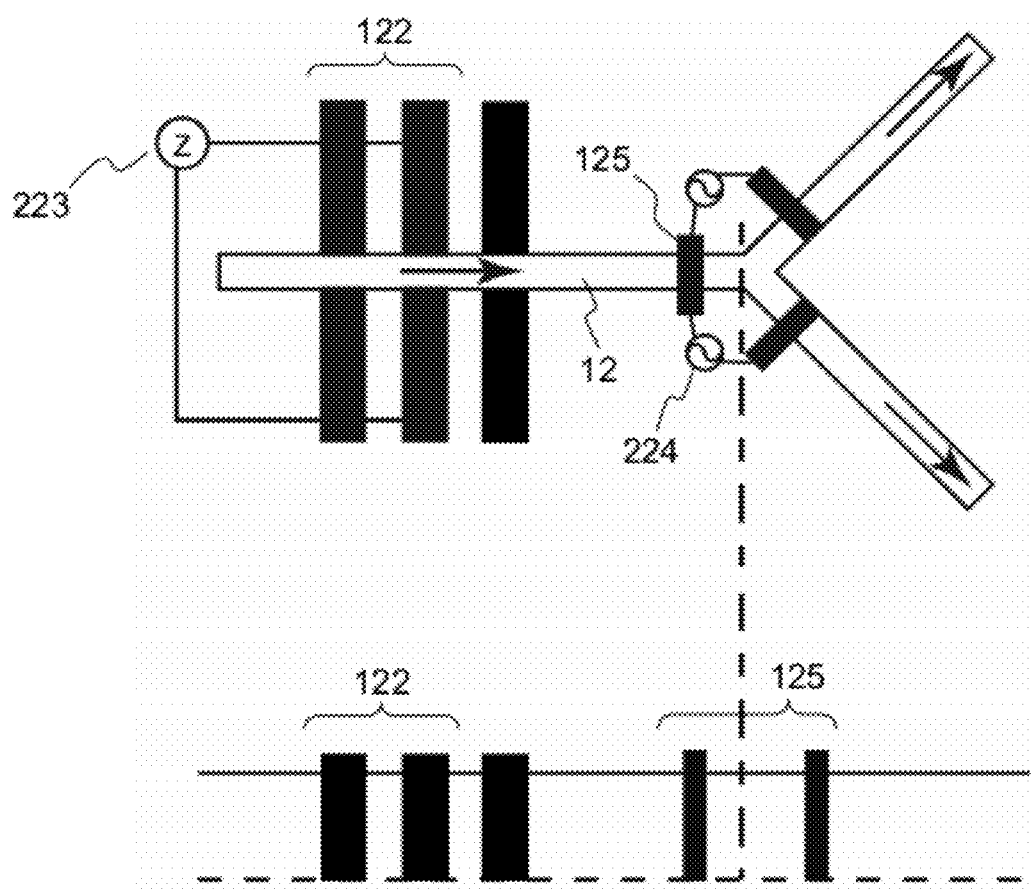
FIG. 12 is a diagram showing a detailed configuration of a nanochannel in a channel device according to the second embodiment as viewed from above.

FIG. 12 is a diagram showing a more detailed configuration of a nanochannel 12 according to the second embodiment. The same components as those in FIG. 2 are denoted by the same reference numerals.

As shown in FIG. 12, the nanochannel 12 may include a plurality of branches and the following may be installed in the nanochannel 12: measuring nanoelectrodes 122 that apply an AC voltage to a molecule passing through a portion of the nanochannel which is not branched, a measurement section 223 that measures the impedance of a molecule between the measuring nanoelectrodes 122, switching nanoelectrodes 125 installed in a branching portion of the nanochannel to guide the molecule to the desired branching channel, and a checking ammeter 224 that measures the impedance of the molecule during switching to check whether the molecule has been guided to the original branching channel. A dielectric constant may be expressed as polarizability (the polarizability of single molecule is the total of local polarizabilities in the internal structure of the molecule and is thus equivalent to the dielectric constant). The point is that a phase shift (retardation or advancement) resulting from application of an AC voltage between the electrodes is measured as the dielectric constant or polarizability.

The measuring nanoelectrodes 122 are preferably formed of a plurality of pairs of electrodes. When a plurality of pairs are provided, a time required for a molecule with its impedance measured by the first electrode pair to reach a downstream electrode pair is measured to enable the flow velocity of the molecule flowing through the nanochannel to be sensed. Then, based on the flow velocity, a time required for the molecule to reach the switching nanoelectrodes 125 can be calculated. Thus, the molecule can be appropriately guided to the desired channel. The switching nanoelectrodes 125, installed in the branching portion of the nanochannel 12, include a common electrode and outlet electrodes provided at respective outlet channels. Each molecule can be guided to the desired channel (switch on) by applying a predetermined voltage (in terms of electric field, an electric field of about several MHz and several MV/m) to between each outlet electrode and the common electrode.

<Circuit Configuration of Molecule Separation Apparatus>

Figure 13:
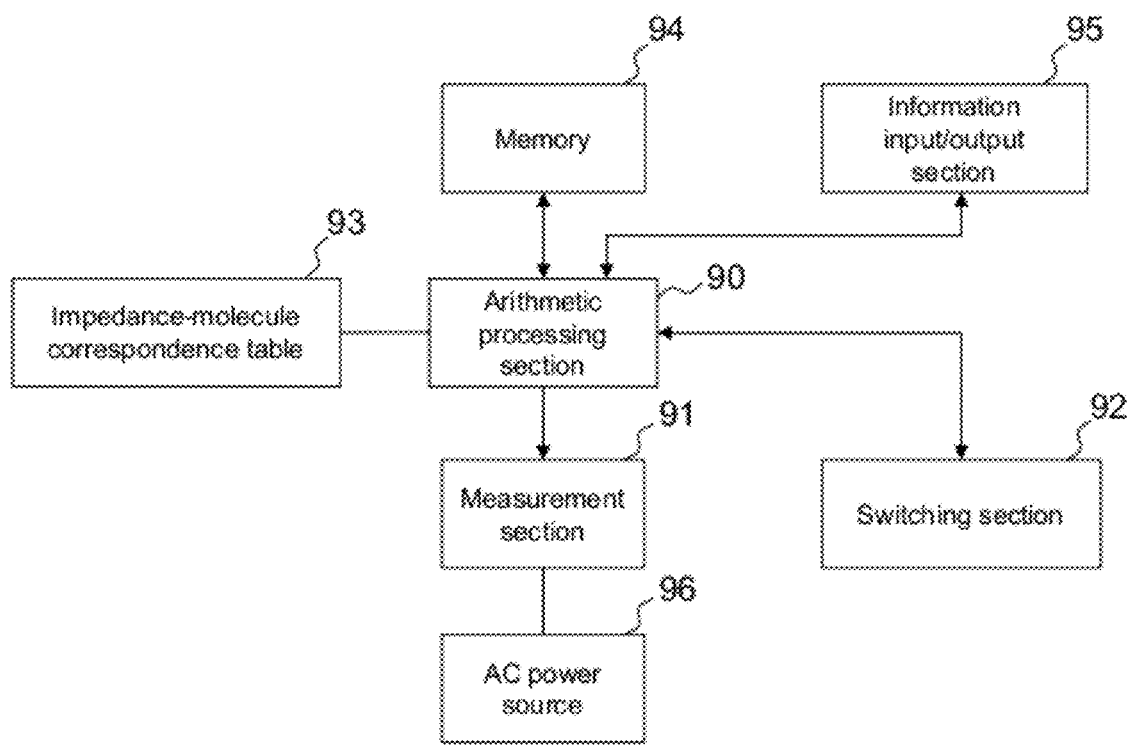
FIG. 13 is a block diagram showing a circuit configuration of a molecule separation apparatus according to the second embodiment of the present invention.

FIG. 13 is a block diagram showing a circuit configuration of the molecule separation apparatus according to the second embodiment of the present invention. The molecule separation apparatus includes a measurement section 91 with an arithmetic processing section 90 that acquires information from components of the apparatus to carry out predetermined calculations in order to control the components as necessary, the measuring nanoelectrodes 122, and the impedance measurement section 223, a switching section 92 with a voltage and frequency variable AC power source 96 that applies an AC voltage to the measuring nanoelectrodes 122 in the measurement section 91, the switching nanoelectrodes 125, a checking ammeter 224, and a voltage application section (not shown in the drawings) which applies a voltage to between each of the electrodes and a common electrode, an impedance-molecule correspondence table 93 showing the correspondence relationship between each of various molecules present between the measuring nanoelectrodes 122 and impedance values obtained when a voltage is applied to a sample containing the various molecules, a memory 44, and an information input/output section 95 to which the user inputs predetermined instructions and the like and which outputs (displays) the results of a separation treatment.

The arithmetic processing section 90 acquires, from the measurement section 91, a resistance value or an impedance value obtained when a molecule passes through the nanochannel 12, and checks the impedance value against the impedance value-molecule correspondence table 93 to identify the type of the passing molecule (the measured resistance value or impedance value is temporarily stored in the memory 94). If a molecule contained in the sample is unknown, the corresponding measured resistance or impedance value is absent from the table 93. Thus, the measured impedance value is stored in the memory 44, and the molecule is separated from the sample with the type of the molecule remaining unknown in accordance with the impedance value.

Furthermore, the arithmetic processing section 90 measures the points of time at which a molecule passes between the electrodes of each of a plurality of electrode pairs of the measuring nanoelectrodes 122 included in the measurement section 91, and calculates the flow velocity of the molecule from the measured point of time and the distances between the electrodes of the electrode pairs. Then, based on the distance from the final electrode pair of the measuring nanoelectrodes 122 to the switching nanoelectrodes 125 and the calculated flow velocity, the arithmetic processing section 90 gives the switching section 92 instructions regarding which of the outlet electrodes of the switching nanoelectrodes is to be subjected to a voltage applied to between the outlet electrode and the common electrode and at which timing the voltage is to be applied. In accordance with the instructions, the molecule is guided to the desired branching channel in the switching section 92, and can thus be separated from the sample.

In the switching section 92, the checking ammeter 224 measures the impedance when the molecule passes by the checking ammeter 224 and supplies the measured value to the arithmetic processing section 90. Then, the arithmetic processing section 90 may compare the impedance value with that measured by the measurement section 91 to check whether the type of the molecule to be separated is correct.

<Operation of Molecule Separation Apparatus>

(1) Sample Injection and Flow Control

First, the user delivers drops of a sample into the injection section 11. The sample contains known and unknown molecules. The molecule separation apparatus can separate the molecules from one another according to type if the sample contains only known molecules, and if the sample contains unknown molecules, can separate these molecules, which exhibit the same impedance value, with the type of the molecules remaining unknown.

In the channel device 10, the substrate 101 is entirely formed of quartz, glass, or the like, and the wall surface of the channel is hydrophilic. Thus, the sample is automatically sucked through the injection section 11 and then through the nanochannel 12 and finally into the output sections 13 and 14 (outlet side) by capillary action. Then, only a very small amount of liquid flows out of the outlet portion, and thus all of an instantaneously outflowing carrier medium evaporates. Hence, in order to compensate for the liquid lost by evaporation, the sample voluntarily continues to flow by capillary action, leading to a given amount of flow in the nanochannel 12.

Furthermore, the flow velocity can be controlled to some degree by cooling the whole or a part of the channel device 10. For example, at a temperature close to the room temperature, all of the sample having left the nanochannel 12 evaporates upon approaching the output sections 13 and 14. Hence, when the whole or a part of the channel device 10 is cooled in order to prevent the evaporation, the sample flows to the outlet. The temperature for cooling may be between about 4° C. and about 25° C. (room temperature).

Here, the capillary action is utilized to introduce the sample into the nanochannel 12. However, the present invention is not limited to this. As described below (variation), the sample can be electrically controlled so as to be introduced into the nanochannel.

(2) Sensing of Single Molecule

Since the width of the nanochannel 12 is of the order of nanometers, each single molecule forming the sample migrates through the nanochannel 12.

In the molecule separation apparatus according to the present invention, the measurement section 91 uses the ammeter 223 to measure the impedance value based on a current flowing between the paired electrodes of the measuring nanoelectrodes 122. When the molecule passes through the measuring nanoelectrodes 122, the impedance changes. Furthermore, even if the molecules are the same in size, the impedance varies depending on the type of the molecule. This nature can be utilized to identify the molecules.

The arithmetic processing section 90 acquires the measured impedance value from the measurement section 91 and stores the acquired impedance value in the memory 94. The arithmetic processing section 90 further checks the impedance value against the impedance value-molecule correspondence table 93. The arithmetic processing section 90 identifies the molecule and continues the separation treatment if the table 93 contains the molecule corresponding to the acquired impedance value. The arithmetic processing section 90 continues the separation treatment without identifying the molecule if the table 93 does not contain the molecule corresponding to the acquired impedance value.

Figure 14:
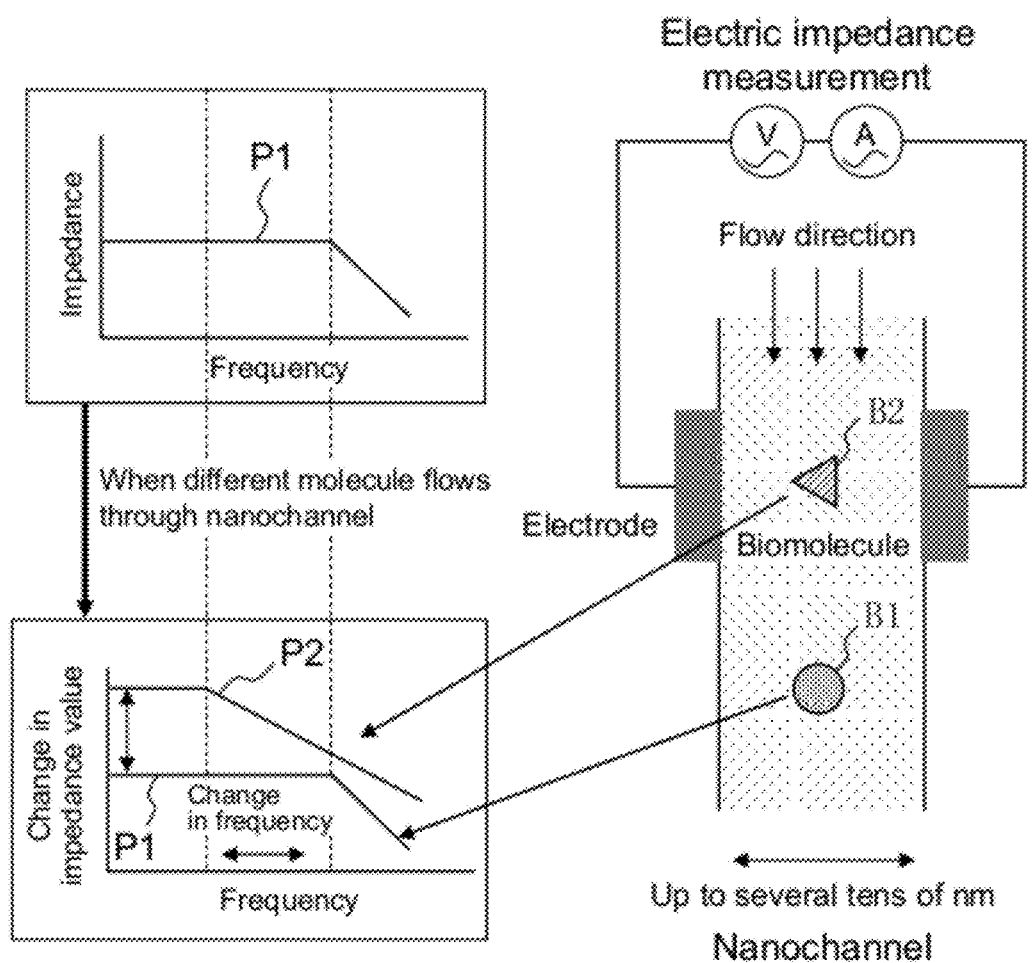
FIG. 14 is a diagram showing an example of a change in impedance value observed when a different molecule (for example, a biomolecule) migrates through the channel.

FIG. 14 is a diagram showing an example of a change in impedance value when a different molecule (for example, a biomolecule) migrates through the channel. As shown in FIG. 14, for example, P1 denotes the property of a change in impedance value resulting from a change in frequency when a biomolecule B1 is present between the measuring nanoelectrodes 122. P2 denotes the property of a change in impedance value resulting from a change in frequency when a biomolecule B2 is present between the measuring nanoelectrodes 122. The change in frequency means sweeping of the frequency of the voltage and frequency variable AC power source within a predetermined range. That is, when the biomolecule B1 is retained between the measuring nanoelectrodes 122 and the frequency of the AC power source is changed, the impedance value measured in association with the change in frequency also changes. This change property is shown at P1 in the graph. The same applies to the biomolecule B2.

If the biomolecules B1 and B2 are almost the same in size, a change in resistance value measured when a DC current is passed between the measuring nanoelectrodes 122 does not vary between the biomolecules B1 and B2. Then, when molecules of different types are almost the same in size, the molecules cannot be identified or separated from the sample. In this regard, proteins typical of the biomolecules are each originally formed of a string-like molecule with 20 types of amino acids strung together (this is referred to as a polypeptide), and the amino acids interact with one another and are voluntarily and regularly folded (this is referred to as folding) to form a three-dimensional conformation. Of course, the internal and general structures vary among the individual molecules. When an external AC electric field is applied to such a biomolecule, the internal local structures are drawn by the external electric field and polarized. However, for example, depending on the frequency, some portions are polarized so as to follow the external electric field, while others fail to follow the external electric field, resulting in retardation (phase difference). The polarizability of the molecule as a whole is determined to be the total of such internal local polarizations. When the polarization property (polarizability) of a single module is measured based on the electric impedance, the individual molecules can be distinguished from one another. Thus, noticing that when molecules are present between the measuring nanoelectrodes 122, a change in impedance varies between the molecules if the molecules are the same in size but are of different types, the present invention utilizes this nature to identify or separate the molecules.

For example, if the types of a plurality of molecules to be identified or separated from the sample are known, the frequency specific to each molecule may be used to measure the impedance value at the frequency, and the molecule corresponding to the impedance value may be identified based on the impedance-molecule correspondence table 43. On the other hand, if the types of a plurality of molecules to be identified or separated from the sample are unknown, first, each molecule is retained between the measuring nanoelectrodes 122, and the frequency of the AC power source is swept to acquire an impedance value change property Pk (k=1, 2, . . . , n) of the molecule. Then, in accordance with each property, the molecule is separated from the sample, and molecules of the same type are guided to a predetermined output section.

If the impedance is insufficiently sensed, the molecules to be identified or separated from the sample may be labeled with a conductive molecule containing, for example, ferrocene. This allows a difference in dielectric constant or electrical conductivity to be emphasized, enabling the impedance to be sensed at a higher sensitivity.

Furthermore, if the measuring nanoelectrodes 122 are formed of a plurality of pairs of electrodes, the arithmetic processing section 40 calculates the migration speed (flow velocity) of (the electrode arrangement area of) the nanochannel 12 based on the time delay of the impedance change at each electrode pair, and further carries out a calculation to determine what seconds later the molecule reaches the branching portion of the nanochannel 12. This allows the migration speed of a particular molecule to be sequentially calculated. Thus, even for a molecule the migration speed of which is unknown, the separation treatment can be appropriately carried out. In the present embodiment, the measuring nanoelectrodes 122 are formed of a plurality of electrode pairs. However, for a molecule the migration speed of which is known, a plurality of electrode pairs need not be provided but installing a single electrode pair suffices.

(3) Switching

As described above, the timing when the molecule to be separated reaches the branching portion of the nanochannel 12 can be determined. Thus, at this timing, the arithmetic processing section 90 applies an electric field to between the common electrode of the switching nanoelectrodes 125 and the outlet electrode on the channel side to which the target molecule is to be guided, depending on the type of the molecule or the impedance value thereof. Then, one of dielectrophoresis, electrophoresis, and an electroosmotic flow acts in the direction of the branching channel to which the molecule is to be guided from the nanochannel, thus allowing the molecule to be guided to the branching channel.

In the present embodiment, the example is illustrated in which the channel device 10 includes the branching channel and the two branching channels branching from the branching channel. However, the present invention is not limited to this. Of course, the number of the branching channels may be equal to the number of the types of the molecules to be separated. Furthermore, a method for providing a plurality of branches (branching channels) branching from the nanochannel may be to provide a plurality of branching channels simultaneously branching from a single branching channel or to cascade bifurcated arrangements together to finally form a plurality of branches. The configuration of the branching channels is not limited.

(4) Electric Measurement of Dynamic State of Conformation of Single Molecule

The molecule separation apparatus according to the second embodiment of the present invention can not only identify or separate different molecule as described above in (2) and (3) but also measure the three-dimensional conformation of a single molecule and the dynamic state thereof. Processing of electrically measuring the dynamic state of three-dimensional conformation of the single molecule will be described.

(i) Necessity of Electric Measurement of Dynamic State

The basic concept of structural biology is that the functions of biomolecules originate from the molecular structure of the biomolecules. Thus, knowing the molecule structure is the shortest way to understand the functions. Even if enormous effort is made to determine a complicated static or quasi-static structure by crystal analysis, NMR, or the like, structures and functions of biomolecules are not successfully understood unless dynamic structural changes resulting from environmental changes (reactant concentration, pH, temperature, ion temperature, and the like), which are the essence of functions of biomolecules, can be clarified. In view of future advancement of molecular biology or structural biology, large-scale application to ptoteome analysis or the functional analysis of proteins for drug discovery, and application to nanobiotechnology for artificial design and creation of molecular machines such as biomolecules, it is essential to develop a technique for sensing the conformation of biomolecules and dynamic changes therein (dynamic state) and a technique for analyzing the functions of biomolecules or identifying the biomolecules, which technique is an application of the sensing technique.

The present invention provides a method for electrically measuring the structure of biomolecules in view of the effects of this method over a wide range from basic research to applications for sensing of the dynamic state of biomolecules.

(ii) Conventional Techniques and Problems Therewith

To analyze biomolecules, analysis techniques such as X-ray diffraction and NMR have been used and have handled molecules in the form of solutions or crystals. When biomolecules are thus handled in the form of a multimolecular system such as a suspension or a solution, information on reactions occurring in the individual molecules and associated structural changes and time responses is lost by averaged random movement among the multiple molecules. On the other hand, crystallization enables a static conformation to be obtained utilizing the periodicity of regularly arranged crystals but causes deviation from physiological environment, resulting in a loss of essential information on the dynamic state such as changes in conformation. That is, the conventional analysis techniques such as X-ray diffraction and NMR are faced with the following dilemma: increased resolution of structural analysis prevents information on the dynamic state from being obtained, whereas an attempt to obtain information on the dynamic state prevents an increase in resolution.

In contrast, it is considered that if manipulation or analysis with focus placed on only single molecule can be carried out, information can be obtained on the dynamics of molecular structures such as structural changes in the individual molecules in an elementary process of reaction and associated time responses. In connection with conventional single-molecule measurement systems, almost all analysis methods for the systems are limited to optical sensing utilizing fluorescent dyes. For example, motion of "movable" proteins such as motor proteins is visualized by fluorescently labeling the proteins or a technique called FRET utilizes transfer of energy between two fluorescent dyes to sense local structural changes. In actuality, these techniques can only sense one portion of single molecule with an enormous amount of time and effort, severely lacks versatility, and cannot be used as general analysis techniques. That is, it is necessary to first determine the conformation by X-ray diffraction and then to obtain primary sequence information on amino acids by electrophoresis or mass analysis. Then, test molecules for observation need to be prepared by carrying out genetic manipulation so as to bind the fluorescent dyes to the sites of particular amino acids. Thus, the test molecules themselves need to be artificially prepared, and natural molecules cannot be used without change.

A molecule separation apparatus according to an embodiment of the present invention allows the conformation of molecules and dynamic changes therein (dynamic state) to be easily measured using natural molecules. The apparatus is the same as that described above in configuration but is different from that in a method for measurement. The method for measurement will be described.

(iii) Principle of Measurement of Changes in Dynamic State of Biomolecules

Figure 15:
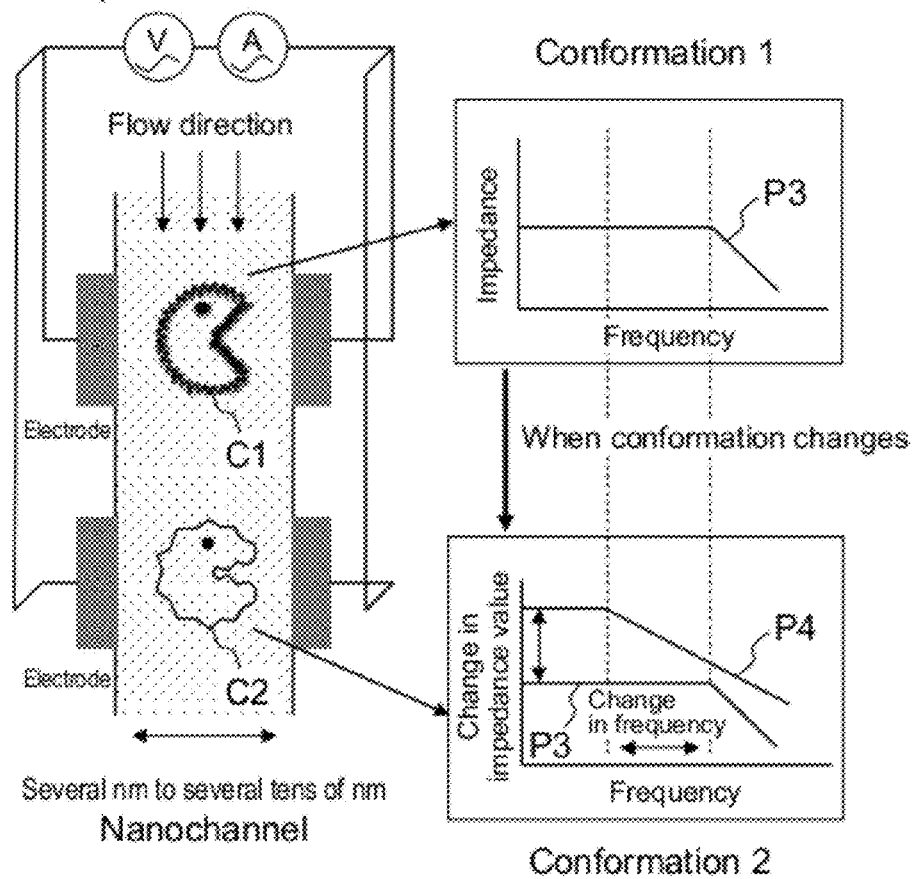
FIG. 15 is a diagram illustrating a principle of sensing of dynamic changes (dynamic state) in the conformation of a biomolecule (example) before and after reaction between the biomolecule and an enzyme.

FIG. 15 is a diagram illustrating the principle of sensing of the structure and dynamic state of molecules before and after the reaction between a biomolecule and an enzyme. In FIG. 15, C1 schematically denotes the structure of a biomolecule before reaction. C2 schematically denotes the structure of the biomolecule during or after the reaction. Furthermore, a property P3 is indicative of an impedance property obtained when the biomolecule located between the measuring nanoelectrodes 122 has the structure C1 and when an AC voltage is applied to between the electrodes, with the frequency swept over a certain range. Similarly, a property P4 is indicative of an impedance property obtained when the same biomolecule located between the measuring nanoelectrodes 122 has the structure C2 and when an AC voltage is applied to between the electrodes, with the frequency swept over a certain range. Thus, even with a single molecule, a change in the structure of the molecule changes the measured impedance value. This nature can be utilized to sense the structure and dynamic state of the molecule in real time.

A dielectrophoretic force is an effect resulting from the interaction between an external electric field and polarization charge induced on the surface of the molecule by the orientation of a dipole in a dielectric (here, the biomolecule) or counter ions in a surrounding solution caused by application of the external electric field to the dielectric. That is, with a sufficient external electric field intensity, if polarization charge induced in only single molecule is utilized to migrate the molecule, then such a change in polarizability as caused by a change in the conformation of the molecule can be sensed by measuring the electric impedance. Moreover, a completely novel method for measurement is conceivable which identifies a molecule or analyzes the dynamics of structure of the molecule by carrying out measurement while using an electrophoretic force to forcibly induce polarization of the molecule or deforming the conformation itself of the molecule, for example, measuring the electric impedance of a higher-order structure such as a protein while destroying and recovering the higher-order structure to a single polypeptide chain that is a primary structure.

(iv) Embodiment of Measurement of the Conformation of a Biomolecule with Conformation Electrically Controlled To allow the dynamic state of structure of a single molecule to be measured, first, a sample into which biomolecules such as DNAs are dissolved is prepared.

Then, the sample is injected into the injection section 10 of the channel device 10 in the molecule separation apparatus, and the DNA molecules are fed through the nanochannel 12 to the measuring nanoelectrodes 122 one by one. The DNA molecule is then retained between the measuring nanoelectrodes 122.

Subsequently, with the voltage value (electric field intensity) of the AC power source fixed to a predetermined value, the frequency is swept over a given range, and the resulting impedance is measured. Furthermore, with the voltage fixed to another value (which is larger than the initial value), the frequency is similarly swept, and the resulting impedance is measured. In this manner, the voltage value of the AC power source is gradually changed, and the frequency is swept at each voltage value. When the dependence of polarizability (dielectric constant) of DNAs on the frequency is utilized, the dielectrophoretic force acts effectively at a particular electric field intensity or higher and at a particular frequency to linearly draw the DNAs from a random coil (see FIGS. 16(a) and 16(b); in an experimental system in FIG. 16, the gap between the electrodes is of micro order for easy observation). Thus, the measurement can be achieved with the molecules forcibly polarized by the dielectrophoretic force or with the conformation itself deformed.

For example, as shown in FIG. 16(c), the impedance is significantly changed when the DNAs are linearly drawn from the random coil at an electric field intensity of at least 3 MV/m and at a frequency of at least 1 kHz. In contrast, sensing the change in impedance value indicates that DNAs have structurally changed from the state of the random coil to the linear state.

Here, the structural change effected by the dielectrophoretic force has been discussed. However, the present invention is not limited to this and also enables sensing (measurement) of a structural change effected by a change in pH, temperature, or ion concentration or enzyme reaction.

(v) Significant Effects Exerted Using Nanochannel

If a wide channel (with a width at least of micro order) is used, when a very small amount of sample with several molecules is measured, the number of molecules to be measured decreases with respect to the number of surrounding water molecules, resulting in a reduced S/N. Furthermore, if molecules in a solution are measured, when a high voltage (in FIG. 16, the order of MV/m) is applied in order to improve measurement sensitivity, the electrodes may disadvantageously be decomposed by electrode reaction.

However, the use of a nanochannel can solve these problems. That is, a substantially reduced measurement space such as a nanochannel can limit the number of water molecules surrounding a single molecule to be measured. This enables suppression of thermal noise caused by thermal motion of water molecules surrounding the target molecule, thus providing an increased sensitivity that cannot be achieved by macro measurement systems. Moreover, the small volume of the nanochannel increases the concentration though the measurement target is actually single molecule.

Furthermore, in an electrode system with a gap length of the order of nanometers, the two layers of an electrical double layer at the interface between the electrode and the solution overlap and are thus substantially negligible, enabling an extremely high sensitivity to be achieved particularly in a low frequency region. Normally, an electrical double layer is inevitably generated at a solid-liquid interface and is included in electrical measurement as a capacitance component, reducing the measurement accuracy. However, such an electrical double layer is absent from a nanometer size system, thus improving absolute accuracy.

Moreover, the electric field intensity is proportional to the electrode interval (electric field intensity V=applied voltage E/gap length d). Thus, a reduced gap length allows an increased electric field to be achieved at the same applied voltage. Hence, the nanogapelectrodes have an extremely short interval and thus provide an electric field intensity of the order of MV/m at a voltage at which no electrolysis occurs as described above.

<Variation>

(1) Sample Introduction Section and the Configuration of a Molecule Separation Apparatus with the Sample Introduction Section (i) A variation of sample introduction may have the same configuration as that described in the first embodiment (see FIG. 5) and will thus not be described below.

Figure 17:
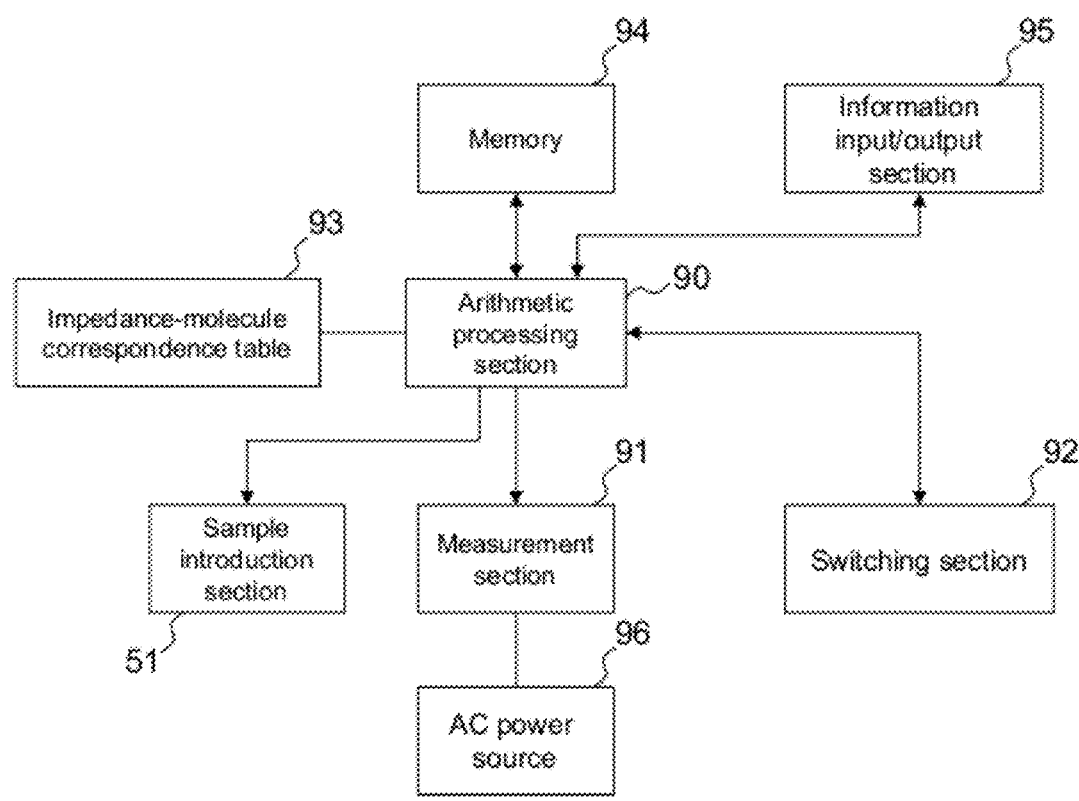
FIG. 17 is a block diagram showing a circuit configuration of a molecule separation apparatus according to a variation of the second embodiment of the present invention.

FIG. 17 is a block diagram showing a circuit configuration of a molecule separation apparatus according to the variation. FIG. 17 is the same as FIG. 13 except that the molecule separation apparatus in FIG. 17 includes a sample introduction section 51. A voltage applied to electrodes in the sample introduction section 51 (the direction of the application, the value of the voltage, and the like) is controlled by the arithmetic processing section 90 in accordance with an instruction input via the information input/output section 95.

(ii) Furthermore, a sample may be introduced utilizing an electroosmotic flow. In this case, a hydrophilic material such as glass is preferably used for the substrate 101 of the channel device 10. Glass is negatively charged, and thus positive ions in the sample are drawn to the negative charges in the glass to form an electrical double layer. When a voltage is applied to the electrical double layer, the charged portion of the sample migrates and the whole sample correspondingly starts to flow. This is the principle of sample introduction using an electroosmotic flow. The surface of the electroosmotic flow may be positively or negatively charged.

(2) Configuration of Nanochannel (Molecule Sensing Area)

Another example of configuration of an area of the nanochannel 12 in the channel device 10 in which the measuring nanoelectrodes 122 are arranged according to the first embodiment (see FIG. 7) is also applicable to the second embodiment.

As described above, the second embodiment uses the measuring nanoelectrodes 122 to sense a molecule flowing through the nanochannel and to calculate the migration speed of the molecule based on a difference in the timing of impedance measurement among the plurality of electrode pairs. In this example, to allow the molecule to be more appropriately identified, the width of the impedance measurement area of the nanochannel is set smaller than that of the remaining area. This makes a change in current caused by the molecule proportional to the volumetric ratio of the volume of the molecule to the volume between the electrodes. Thus, the volumetric ratio increases with decreasing volume between the electrodes. This increases the magnitude of a change in impedance caused by the molecule, allowing sensitive measurement to be achieved.

III. Example of Manufacture of Channel Device

An example of a method for manufacturing the channel device for use in the first and second embodiments will be described below.

(1) Manufacturing Steps

Figure 18:
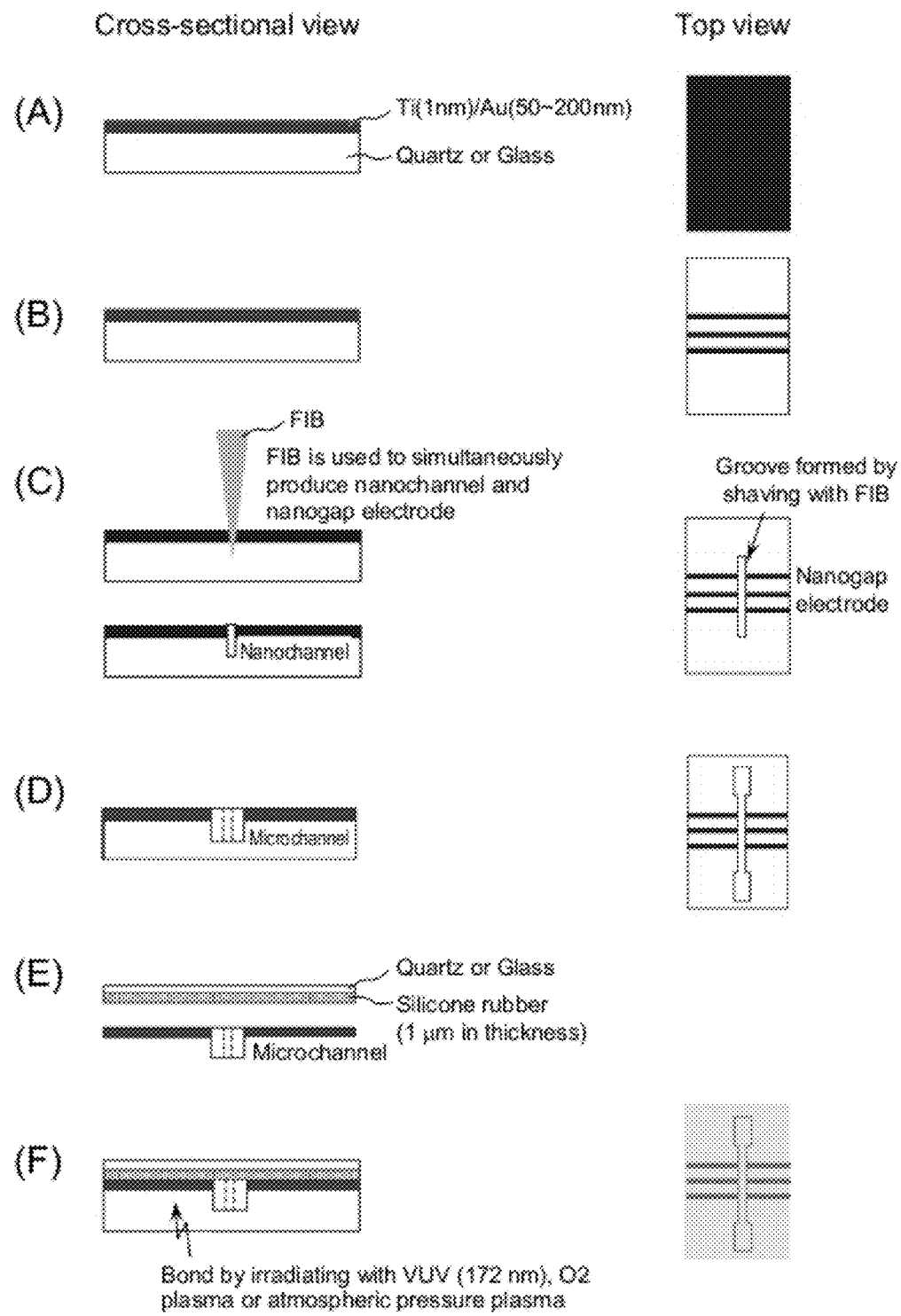
FIG. 18 is a diagram illustrating steps of manufacturing a channel device according to the present invention.

FIG. 18 is a diagram illustrating the steps of manufacturing the channel device 10 according to the present invention.

Step 1: Titanium is vacuum-deposited on a substrate formed of quartz or glass to a thickness of, for example, 1 nm, and gold is vacuum-deposited on the titanium to a thickness of, for example, 50 to 200 nm. The gold is a material of electrodes, and the titanium functions as an adhesive for bonding the gold and the substrate together. Thus, the electrode material is deposited on the substrate (see FIG. 18(A)).

Step 2: A normal photolithography technique is used to pattern the nanoelectrode portion (for example, the portion corresponding to the above-described nanoelectrodes 122) (see FIG. 18(B)).

Step 3: A focusing ion beam (FIB) or reactive ion etching (RIE) is used to shave the substrate with the nanoelectrode pattern produced in step 2 to produce a groove (nanochannel). The nanoelectrode pattern is simultaneously shaved to simultaneously produce electrode pairs (see FIG. 18(C)).

Step 4: An end of the nanochannel produced in step 3 is further shaved to produce a microchannel (corresponding to the above-described injection section 11) (see FIG. 18(D)).

Step 5: Silicon rubber is coated, by spin coating, on the quartz or glass to a thickness of, for example, 1 μm and then heated to, for example, 150° C. and fixed to produce a lid member (see FIG. 18(E)).

Step 6: The lid member produced in step 5 is placed on the channel member produced in step 4 and is irradiated with one of vacuum UV light (wavelength: 172 nm), oxygen plasma, and atmospheric pressure plasma so as to be bonded to the channel member (see FIG. 18(F)).

(2) Channel Shape

Figure 19:
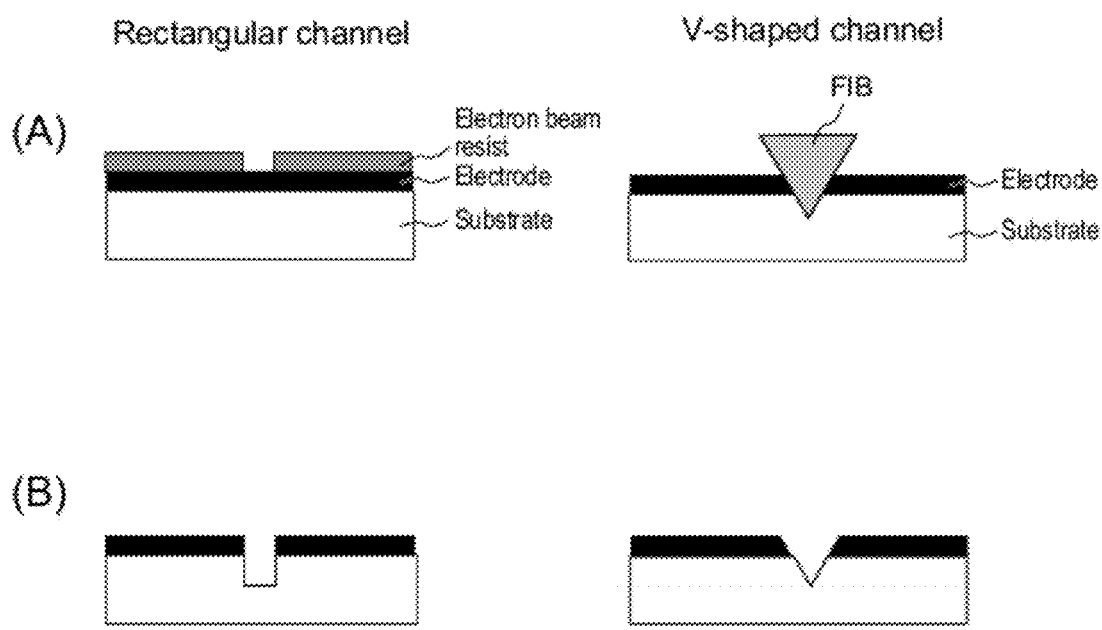
FIG. 19 is a diagram illustrating steps of forming a rectangular channel and a V-shaped channel.

FIG. 19 is a diagram illustrating a method for producing a differently shaped channel. The present invention discusses channels with a rectangular cross section and a V-shaped cross section. However, the rectangular channel need not be exactly rectangular but may have a round bottom surface. Furthermore, V-shaped channel need not be exactly V-shaped but may be, for example, smaller in channel width toward the bottom surface of the channel.

For the rectangular channel, an electron beam resist is formed on the substrate with the electrode pattern formed in the above-described step 2 (see FIG. 19(A)). The substrate is shaved using reactive ion etching (RIE) to form a channel of a nanometer size (see FIG. 19(B)).

On the other hand, for the V-shaped channel, the substrate with the electrode pattern formed in the above-described step 2 is irradiated with an focused ion beam (FIB) and thus shaved and processed (see FIG. 19(A)). The focused ion beam is focused on one point to form a groove shaped along a beam profile (V shape), on the substrate (see FIG. 19(B)).

(3) Electrode Pattern

FIG. 20 is a diagram illustrating different electrode patterns formed on the substrate. FIG. 20(A) is a diagram showing a pattern 1 in which the electrode pattern only reaches a channel edge. FIG. 20(B) is a diagram showing a pattern 2 in which the electrode pattern extends into the interior of the channel.

In the pattern 1, the electrode is present only on the surface of the substrate, and thus a line of electric force (electric field) generated between the electrodes does not travel to the bottom of the channel. Thus, the pattern 1 has difficulty of measuring the resistance or impedance of a passing molecule at the bottom of the channel.

On the other hand, in the pattern 2, the electrode is formed so as to cover the side surfaces of the channel. Consequently, the pattern 2 allows a uniform electric field to be formed even at the bottom of the channel. The pattern 2 thus allows the resistance or impedance of a passing molecule to be measured even at the bottom of the channel.

(4) Formation of an Electrode Pattern

FIG. 21 is a diagram illustrating a step of forming the electrode patterns 1 and 2 shown in FIG. 20 and specifically illustrating the details of step 3 shown in FIG. 18(C).

Step 3-1: The substrate with the electrodes patterned on the surface thereof is prepared (see FIG. 21(A)). A groove is vertically dug in the substrate by reactive etching (RIE) or etched by a focused ion beam (FIB) (see FIG. 21(B)). The pattern 1 (FIG. 20(A)) may be produced by completing the above-described steps. To produce the pattern 2 (FIG. 20(B)), the following steps are continuously carried out.

Step 3-2: Reactive etching is further applied to the substrate with an etching condition (for example, a plasma pressure) varied between the rectangular channel and the V-shaped channel. Then, the substrate can further be shaved in the vertical and horizontal directions to form a groove. Thus, the electrode pattern is left so as to extend beyond the edge portion of the channel (overhung) (see FIG. 21(C)).

Step 3-3: The substrate produced in step 3-3 is, for example, dipped in water and then lifted from the water. When the wet substrate is dried, the overhung portions of the electrodes are attracted to the side surfaces of the channel by surface tension. This results in a configuration in which the electrode pattern covers the side surfaces of the channel (see FIG. 21(D)).

(5) Coating of the Electrodes with Insulating Film

FIG. 22 is a diagram showing that an insulating film is coated on the electrode pattern.

When the channel device is in use, the electrode pattern provided in the nanochannel directly contacts the sample. Thus, the metal forming the electrodes may be melted into the sample. In this regard, if a DC voltage is applied to the electrodes and the resulting resistance is measured (first embodiment), the electrodes need to contact the sample, and thus the electrode pattern cannot be covered with a protective film or the like. However, if an AC voltage is applied to the electrodes and the resulting impedance is measured (second embodiment), the direct contact of the electrodes with the sample is less needed with increasing frequency. Thus, the surface of the electrode pattern may be coated with the insulating film so that the impedance can be measured across the insulating film. This enables the electrodes from being melted by electrolytic reaction.

The insulating film can be formed by, for example, sputtering $SiO_2$ or $Si_3N_4$ on the electrode pattern to deposit a film of thickness several nm to several hundreds nm on the electrode pattern.

(6) Comparison between Rectangular Channel and V-Shaped Channel

FIG. 23 is a diagram showing a comparison of features between the rectangular channel and the V-shaped channel (the electrode pattern is not present on the side surfaces of the nanochannel).

First, the range of the nanochannel which can be subjected to electric measurement is examined with reference to FIG. 23(A). The rectangular channel has many areas that cannot be reached by a line of electric force (electric field). In particular, no electric field is present in the corners of the bottom surface of the channel. On the other hand, in the V-shaped channel, a line of electric force fails to reach the V-shaped tip of the nanochannel. However, the V-shaped channel as a whole has fewer areas with no electric field present therein than the rectangular channel.

Now, the (depth-wise) position in the nanochannel where a molecule flows is examined with reference to FIG. 23(B). In the rectangular channel, the width of the bottom surface portion of the channel is larger than the diameter of the molecule. Thus, the molecule often flows in the bottom surface portion. On the other hand, in the V-shaped channel, the nanochannel is narrower in the depth direction, and thus the molecule only infrequently flows in an area with no electric field present therein.

Hence, as seen in FIGS. 23(A) and 23(B), in the V-shaped channel, the density of lines of electric force is higher with respect to the cross section of the channel, and the measurement area accounts for a high percentage of the entire cross section of the channel. Furthermore, the V-shaped channel is narrower in the bottom portion, and molecules contained in the sample are unlikely to flow in the bottom portion and likely to flow only in the measurement area.

If the electrode pattern is present on the side surfaces of the nanochannel (see FIGS. 20(B) and 21(D)), the above-described problem is solved even for the rectangular channel.

(7) Actual Channel

FIG. 24 is a diagram showing an actual channel device produced in accordance with the above-described method for manufacture. As seen in FIG. 24, the channel device includes one injection section, a nanochannel formed of one nanochannel and three branching channels, and three output sections (molecule speed measurement electrodes, single-molecule identification electrodes (measuring nanoelectrodes), and electrodes for distribution among the branching channels (switching nanoelectrodes)).

IV. Conclusion (1) Molecules that can be identified or separated from a sample according to the present invention are molecules of a nanometer size, for example, biomolecules such as DNAs, RNAs, proteins in general, polypeptides, amino acids, polysaccharides, lipids, cytokines, signal transducers, and hormones. Molecules other than the biomolecules which can be identified or separated from a sample include general organic polymers, for example, synthetic resins such as polyethylene, polycarbonate, and acrylic, synthetic fibers such as nylon and vinyl, and silicone resins, as well as inorganic polymers. Moreover, particulate substances of a nanometer size, for example, colloids and nanoparticles can be identified or separated from a sample.

(2) The sample treatment apparatus according to the present invention can be utilized for any biological industries. The sample treatment apparatus according to the present invention can be utilized for applications, for example, medical applications such as examination of diseased cells, sensing of pathogenic bacteria, a portable sensor for monitoring of insulin or the like, extraction of effective substances from cells of plants and animals, on-site blood examination chips, pathological examination chips (examination of a sample other than the blood), portable human body monitoring (monitoring of body conditions), artificial organ sensors, on-site infection test chips, and toxicology test chips, drug discovery applications such as testing of effects of new drugs for drug discovery (drug manufacture), drug test chips, and administration result analysis chips, environmental applications such as sensing of virulent bacteria, environments: examination of pathogenic bacteria, biohazard measurement chips, and on-site measurement of biological contamination in environments (O-157 and the like), applications in life science such as exhaustive protein analyses in general such as proteomics, biochemistry: structural analysis of proteins, biochemical reaction analyses in general, and every field of exhaustive protein analysis such as sequencing, proteome, transcriptome analysis, and epigenetics of DNAs and proteins, applications in the field of food hygiene such as hygiene monitoring (monitoring of growth of virulent bacteria and the like), monitoring of production (monitoring of the conditions of fermentations in general (beer, cheese, and the like)), contamination test chips (monitoring of O-157, BSE, and the like), and monitoring of activity of yeasts in fermentation apparatuses, and applications such as blood test chips that can be used like band-aids (pregnancy testing, diabetes testing, and sensing systems based on measurement of any protein).

(3) In the first embodiment, a change in resistance is measured when a molecule is migrated between the electrodes of the electrode pair installed in the nanochannel. Then, the arithmetic processing section identifies the molecule based on the resistance value measured by the resistance measurement section. Thus, a single molecule is migrated through the nanochannel, information is acquired which is indicative of a change in resistance resulting from passage of the molecule between the paired electrodes, and the molecule is identified based on the information. Thus, the molecule can be accurately identified, and the use of the nanochannel enables the apparatus to be miniaturized.

The nanochannel includes the branching portion and the plurality of branching channels extending from the branching portion to the respective output sections. The identified molecule is guided from the main channel to the desired one of the plurality of branching channels. The treatment of guiding the molecule is carried out by the common electrode provided on the main channel side, the plurality of outlet electrodes provided on the respective branching channels, the voltage application section that applies a voltage to the common electrode and each of the plurality of outlet electrodes, and the switching section that selects a pair of the common electrode and one of the outlet electrodes. Based on information on the identified molecule, the arithmetic processing section determines a pair of the common electrode and the outlet electrode and controllably applies a voltage to the pair. This allows the desired molecule to be accurately acquired separately from the other molecules.

Furthermore, in the first embodiment, the channel device includes the injection section from which the sample to be treated is injected (in the present embodiment, the injection section has a width and a depth both of micrometer order, but the present invention is not limited to this order provided that the sample can be injected from the injection section), the nanochannel having a width and a depth both of a nanometer order and through which a molecule contained in the sample is migrated, and the plurality of output sections to which the molecule having migrated through the nanochannel is guided and from which the molecule is then taken out. Moreover, the nanochannel includes the branching portion and the plurality of branching channels extending from the branching portion to the respective output sections. A voltage is applied to between the electrodes of the electrode pair installed in the nanochannel, and a resistance is measured when the molecule migrates between the electrodes. Furthermore, the arithmetic processing section associates the measured resistance value with the molecule. The molecule associated with the measured current value (impedance value) is guided from the nanochannel to the desired one of the plurality of branching channels. The guiding treatment is carried out by the common electrode provided on the main channel side, the plurality of outlet electrodes provided on the respective branching channels, the voltage application section that applies a voltage to the common electrode and each of the plurality of outlet electrodes, and the switching section that selects a pair of the common electrode and one of the outlet electrodes. Thus, even if the types of the molecules contained in the sample are unknown, each molecule can be separated from the sample based on the resistance value obtained when the molecule passes by the measuring nanoelectrodes.

In the above-described sample treatment apparatus, a plurality of electrode pairs may be provided in the nanochannel and arranged at predetermined intervals. In this case, the measurement section measures the resistance when the molecule passes through each electrode pair. Furthermore, the arithmetic processing section calculates the migration speed of the molecule based on a difference in the time when the resistance value is measured, and controls the timing for applying a voltage (or an electric field) based on the calculated migration speed of the molecule.

Furthermore, in the above-described apparatus, the channel device is formed of a hydrophilic insulator material. In this case, the sample is introduced from the injection section into the nanochannel by capillary action. The utilization of the capillary action further simplifies the apparatus configuration, enabling the apparatus to be miniaturized. Alternatively, one of new paired electrodes may be arranged in the injection section, and the other may be arranged in the nanochannel. In this case, an electric field is generated between the paired electrodes to guide the sample from the injection section into the nanochannel. The flow can be electrically controlled, enabling more accurate measurement.

(4) In the second embodiment, an AC voltage is applied to between the electrodes of the electrode pair installed in the nanochannel, and the impedance is measured when a molecule is present between the electrodes. Then, the arithmetic processing section identifies the molecule based on the measured impedance value. Thus, a single molecule is migrated through the nanochannel, information is acquired which is indicative of a change in impedance resulting from the presence of the molecule between the paired electrodes, and the molecule is identified based on the information. Thus, the molecule that are the same in molecular size but different in type can be accurately identified, and the use of the nanochannel enables the apparatus to be miniaturized.

The nanochannel includes the branching portion and the plurality of branching channels extending from the branching portion to the respective output sections. The identified molecule is guided from the nanochannel to the desired one of the plurality of branching channels. The treatment of guiding the molecule is carried out by the common electrode provided on the nanochannel side, the plurality of outlet electrodes provided on the respective output channels, the voltage application section (electric field application section) that applies a voltage (electric field) to the common electrode and each of the plurality of outlet electrodes, and the switching section that selects a pair of the common electrode and one of the outlet electrodes. Based on information on the identified molecule, the arithmetic processing section determines a pair of the common electrode and the outlet electrode and controllably applies a voltage to the pair. This allows the desired molecule to be accurately separated from the other molecules.

Furthermore, in the second embodiment, the channel device includes the injection section having a width and a depth both of micrometer order and from which the sample to be treated is injected, the nanochannel having a width and a depth both of nanometer order and through which a molecule contained in the sample is migrated, and the plurality of output sections into one of which the molecule having migrated through the nanochannel is separately guided. The nanochannel includes the plurality of branching channels connected via the branching portion to the respective output sections. An AC voltage is applied to between the electrodes of the electrode pair installed in the nanochannel, and the impedance is measured when the molecule is present between the electrodes. Furthermore, the arithmetic processing section associates the measured impedance value with the molecule. The molecule associated with the measured impedance value is guided from the nanochannel to the desired one of the plurality of branching channels. The guiding treatment is carried out by the common electrode provided on the nanochannel side, the plurality of outlet electrodes provided on the respective branching channels, the voltage application section (electric field application section) that applies a voltage to the common electrode and each of the plurality of outlet electrodes, and the switching section that selects a pair of the common electrode and one of the outlet electrodes. Thus, even if the types of the molecules contained in the sample are unknown, each molecule can be separated from the sample based on the impedance value obtained when the molecule passes by the measuring nanoelectrodes.

In the above-described sample treatment apparatus, a plurality of electrode pairs may be provided in the nanochannel and arranged at predetermined intervals. In this case, the measurement section measures the impedance when the molecule passes through each electrode pair. Furthermore, the arithmetic processing section calculates the migration speed of the molecule based on a difference in the time when the impedance value is measured, and controls the timing for applying a voltage (electric field) based on the calculated migration speed of the molecule.

Furthermore, in the above-described apparatus, the substrate of the channel device is formed of a hydrophilic insulator material. In this case, the sample is introduced from the injection section into the nanochannel by capillary action. The utilization of the capillary action further simplifies the apparatus configuration, enabling the apparatus to be miniaturized. Alternatively, as described above, one of new paired electrodes may be arranged in the injection section, and the other may be arranged in the nanochannel. In this case, an electric field is generated between the paired electrodes to guide the sample from the injection section into the nanochannel.

Moreover, the molecule (biomolecule) is retained between the paired electrodes, and the environment of the molecule is changed (the molecule is allowed to react with an enzyme, the temperature is changed, the pH is changed, the ion concentration is changed, or the like). Furthermore, with the frequency of the AC power source varied, the impedance is measured when an AC voltage is applied to between the electrodes. Then, based on the measured impedance value, the conformation of the molecule and the dynamic state thereof are sensed. For the AC power source, not only the frequency but also the voltage to be applied to between the paired electrodes in the nanochannel is variable. In this case, with the frequency and voltage of the AC power source varied, the impedance is measured, and based on changes in impedance value occurring when the frequency and voltage of the AC power source are changed, the conformation of the molecule and dynamic changes therein (dynamic state) are sensed. This enables a change in the structure of a molecule (particularly a biomolecule) to be dynamically determined, thus allowing the functions of the molecule to be determined.

(5) The above-described embodiments illustrate the aspect in which the channel device includes the one injection section 11 and the plurality of output sections 14. However, the channel device may include a plurality of injection sections and a plurality of output sections. In this case, the channel device is formed of the plurality of injection sections, a plurality of injection channels extending from the respective injection sections to one nanochannel, the nanochannel, a plurality of branching channels, and the plurality of output sections. In another possible aspect, the channel device includes only one injection section and one output section. In this case, the channel device is formed of the one injection section, one nanochannel, and the one output section. This channel device is utilized, for example, to check whether or not the sample contains one particular molecule.

REFERENCE SIGNS LIST

M . . . Molecule
AS . . . AC power source
E1, E2, E3, E4, E5, E6 . . . Electrodes
10 . . . Channel device
11 . . . Injection section
12 . . . Nanochannel
12a, 12b, 21c . . . Branching channels
13 . . . Output section
14 . . . Output section
15 . . . Glass
16 . . . Adhesive member
40 . . . Arithmetic processing section
41 . . . Measurement section
42 . . . Switching section
43 . . . Current value-molecule correspondence table
44 . . . Memory
45 . . . Information input/output section
51 . . . Sample introduction section
90 . . . Arithmetic processing section
91 . . . Measurement section
92 . . . Switching section
93 . . . Impedance-molecule correspondence table 94 ... Memory
95 ... Information input/output section
96 ... AC power source
101 ... Substrate
122 ... Measuring nanoelectrodes
123 ... Ammeter
124 ... Ammeter
223 ... Impedance measurement section
224 ... Checking impedance measurement section
125 ... Switching nanoelectrodes
511 ... Electrode
512 ... Electrode
513 ... Electrode

The invention claimed is:

1. A channel device comprising:
a nanosize channel through which a sample solution containing a molecule flows;
at least one electrode pair arranged near the nanosize channel; and
an AC power source that applies an AC voltage to the electrodes,
wherein the electrode pair is covered with an insulator material so as not to contact the sample solution flowing through the nanosize channel, and
a portion of the nanosize channel in which the electrode pair is arranged is configured to be smaller in width than the entire nanosize channel except for the portion in which the electrode pair is arranged.

2. A channel device comprising:
a nanosize channel through which a sample solution containing a molecule flows;
a branching portion;
a plurality of branching channels branching from the nano size channel in the branching portion;
and an electrode pair,
wherein the electrode pair is arranged so as to sandwich the nanosize channel between the electrodes,
the electrode pair is covered with an insulator material so as not to contact the sample solution flowing through the nanosize channel, and
a portion of the nanosize channel in which the electrode pair is arranged is configured to be smaller in width than the entire nanosize channel except for the portion in which the electrode pair is arranged.

3. The channel device according to claim 2, wherein an electrode pair different from the electrode pair arranged in the nanosize channel is further arranged near the branching channels, and
the electrode pair arranged near the branching channels is covered With an insulator material so as not to contact the sample solution flowing through the nanosize channel.

4. The channel device according to claim 2, wherein each of the branching channels has a cross section of a nanometer size.

5. A sample treating apparatus comprising:
a channel device with a nanosize channel through which a sample solution containing a molecule flows and a least one electrode pair arranged in the nanosize channel;
an AC power source that applies an AC voltage to the electrodes; and
a measurement circuit that identifies one molecule contained in the sample flowing through the channel,
wherein the electrode pair is covered with an insulator material so as not to contact the sample solution flowing through the nanosize channel, and
a portion of the nanosize channel in which the electrode pair is arranged is configured to be smaller in width than the entire nanosize channel except for the portion in which the electrode pair is arranged.

6. A sample treatment apparatus comprising:
a channel device and a switching section,
wherein the channel device comprises a nanosize channel through which a sample solution containing a molecule flows;
a branching portion;
a plurality of branching channels branching from the nano size channel in the branching portion; and
a first electrode pair and a second electrode pair,
the first electrode pair is arranged so as to sandwich the nanosize channel between the electrodes, and the second electrode pair that is different from the first electrode pair arranged in the nanosize channel is arranged at the branching channels,
the first and second electrode pairs are covered with an insulator material so as not to contact the sample solution flowing through the nanosize channel,
a portion of the nanosize channel in which the first electrode pair is arranged is configured to be smaller in width than the entire nanosize channel except for the portion in which the first electrode pair is arranged, and
the switching section electrically stimulates one molecule contained in the sample solution via the second electrode pair to urge the molecule to perform mechanism behavior in such a manner that the dynamic behavior allows the molecule to be guided to a predetermined one of the branching channels.

7. The channel device according to claim 6, wherein each of the branching channels has a cross section of a nanometer size.

8. A sample treatment apparatus identifying a molecule contained in a sample solution, the sample treatment apparatus comprising:
a channel device comprising an injection section from which the sample solution is injected and a nanosize channel having a cross section of a nanometer order size and through which the molecule contained in the sample solution is allowed to migrate;
a measurement circuit which applies a voltage to between electrodes of an electrode pair installed in the nanosize channel and which measures impedance when the molecule passes between the electrodes; and
an arithmetic processing circuit that identifies the molecule based on the impedance value measured by the measurement circuit,
wherein the electrode pair is covered with an insulator material so as not to contact the sample solution flowing through the nanosize channel, and
a portion of the nanosize channel in which the electrode pair is arranged is configured to be smaller in width than the entire nanosize channel except for the portion in which the electrode pair is arranged.

9. The sample treatment apparatus according to claim 8, further comprising:
a plurality of output sections from which the molecule having migrated through the nanosize channel is taken out; and
a molecule separation circuit that separates the identified molecule from the sample,
wherein the nanosize channel comprises a branching portion located beyond the nanosize channel and a plurality of branching portions connecting from the branching portion to the respective output sections, and the molecule separation circuit guides the identified molecule from the nanochannel to a predetermined one of the plurality of branching channels.

10. The sample treatment apparatus according to claim 9, wherein the molecule separation circuit comprises:
   a plurality of output electrodes provided at the respective plurality of branching channels,
   a predetermined electrode comprising an electrode pair provided on the nanochannel side or a common electrode shared among the plurality of outlet electrodes,
   a switching section that applies a voltage to the predetermined electrode pair or to the predetermined electrode and one of the plurality of outlet electrodes and selects i) the predetermined electrode pair or ii) the electrode pair of the predetermined electrode and one of the plurality of outlet electrodes, and
   the arithmetic processing circuit selects one of the electrode pairs based on information on the identified molecule, and controls the molecule separation circuit in such a manner that the voltage is applied to the determined electrode pair.

11. The sample treatment apparatus according to claim 10, wherein a plurality of electrode pairs are provided in the nanosize channel and arranged at predetermined intervals,
   the measurement circuit measures the impedance when the molecule passes through each of the electrode pairs, and
   the arithmetic processing circuit calculates a migration speed of the molecule based on a difference in a time when the impedance value is measured, and controls a timing for applying the voltage based on the calculated migration speed of the molecule.

12. The sample treatment apparatus according to claim 8, wherein the channel device is formed of a hydrophilic insulator material, and
   the sample solution is introduced from the injection section into the nanosize channel by capillary action.

13. The sample treatment apparatus according to claim 8, wherein one of the paired introducing electrodes that apply a voltage to the sample solution is arranged in the injection section, and the other is arranged in the nanosize channel, and
   an electric field is generated between the paired introducing electrodes, wherein the electric field generates an electroosmotic flow in the vicinity of an inlet side of the channel device to introduce the sample solution from the injection section into the nanosize channel.

14. The sample treatment apparatus according to claim 8, wherein the injection section has a cross-sectional size of micrometer order.

15. The sample treatment apparatus according to claim 8, further comprising an AC power source that applies an AC voltage to between the electrodes of the electrode pair installed in the nanosize channel,
   wherein the measurement circuit measures the impedance when the molecule passes between the paired electrodes.

16. The sample treatment apparatus according to claim 15, wherein the AC power source is variable in frequency, and
   the measurement circuit measures the impedance when the frequency of the AC power source is changed within a predetermined range.

17. The sample treatment apparatus according to claim 15, further comprising:
   a plurality of output sections from which the molecule having migrated through the nanosize channel is taken out; and
   a molecule separation circuit that separates the identified molecule from the sample,
   wherein the nanosize channel comprises a branching portion located beyond the nanosize channel and a plurality of branching portions connecting from the branching portion to the respective output sections, and
   the molecule separation circuit guides the identified molecule from the nanochannel to a desired one of the plurality of branching channels.

18. The sample treatment apparatus according to claim 17, wherein the molecule separation circuit comprises:
   a predetermined electrode formed of an electrode pair provided on a nanochannel side or a common electrode,
   a plurality of outlet electrodes provided at the respective plurality of branching channels,
   a voltage application section that applies a voltage to the predetermined electrode pair or to the predetermined electrode and one of the plurality of outlet electrodes, and
   a switching section that selects i) the predetermined electrode pair or ii) the pair of the predetermined electrode and one of the plurality of outlet electrodes, and
   the arithmetic processing circuit selects the pair based on information on the identified molecule, and controls the molecule separation circuit in such a manner that the voltage is applied to the determined pair.

19. The sample treatment apparatus according to claim 18, wherein a plurality of electrode pairs are provided in the nanosize channel and arranged at predetermined intervals,
   the measurement circuit measures the impedance when the molecule passes through each of the electrode pairs, and
   the arithmetic processing circuit calculates a Migration speed of the molecule based on a difference in a time when the impedance value is measured, and controls a timing for applying the voltage based on the calculated migration speed of the molecule.

20. The sample treatment apparatus according to claim 15, wherein the channel device is formed of a hydrophilic insulator material,
   and the sample solution is introduced from the injection section into the nanosize channel by capillary action.

21. The sample treatment apparatus according to claim 15, wherein one of the paired introducing electrodes that apply a voltage to the sample solution is arranged in the injection section, and the other is arranged in the nanosize channel, and
   an electric field is generated between the paired introducing electrodes, wherein the electric field generates an electroosmotic flow m the vicinity of an inlet side of the channel device to introduce the sample solution from the injection section into the nanosize channel.

22. The sample treatment apparatus according to claim 17, wherein the injection section and the plurality of output sections each have a cross-sectional size of micrometer order.

23. A sample treatment apparatus separating a predetermined molecule contained in a sample solution, the sample treating apparatus comprising:
   a channel device comprising
      an injection section from which a sample solution is injected,
      a nanosize channel having a cross section of a nanometer order size and through which the molecule contained in the sample is allowed to migrate, and
      a plurality of output sections from which the molecule having migrated through the nanosize channel is taken out,
      the nanosize channel comprising a branching portion located beyond the nanosize channel and a plurality of branching channels connecting from the branching portion to the respective plurality of output sections;

a measurement circuit which applies a voltage to between electrodes of an electrode pair installed in the nanosize channel and which measures resistance or impedance when the molecule passes between the electrodes;

an arithmetic processing circuit associates the molecule with the resistance value or impedance value measured by the measurement circuit; and a molecule separation circuit guides the molecule associated with the measured resistance value or impedance value from the nanosize channel to a desired one of the plurality of branching channels, wherein in the channel device, the electrode pair is covered with an insulator material so as not to contact the sample solution flowing through the nanosize channel, and a portion of the nanosize channel in which the electrode pair is arranged is configured to be smaller in width than the entire nanosize channel except for the portion in which the electrode pair is arranged.

24. The sample treatment apparatus according to claim 23, wherein the molecule separation circuit comprises:
 a predetermined electrode formed of an electrode pair provided on a nanosize channel side or a common electrode,
 a plurality of outlet electrodes provided at the respective plurality of branching channels,
 a switching section that applies a voltage to the predetermined electrode pair or to the predetermined electrode and one of the plurality of outlet electrodes, and selects i) the predetermined electrode pair or ii) the pair of the predetermined electrode and one of the plurality of outlet electrodes, and
 the arithmetic processing circuit selects the pair based on information on the measured resistance value or impedance value, and controls the molecule separation circuit in such a manner that the voltage is applied to the determined pair.

25. The sample treatment apparatus according to claim 24, wherein a plurality of electrode pairs are provided in the nanosize channel and arranged at predetermined intervals,
 the measurement circuit measures the resistance or impedance when the molecule passes through each of the electrode pairs, and
 the arithmetic processing circuit calculates a migration speed of the molecule based on a difference in a time when the resistance value or the impedance value is measured, and controls a timing for applying the voltage based on the calculated migration speed of the molecule.

26. The sample treatment apparatus according to claim 23, wherein the channel device is formed of a hydrophilic insulator material, and
 the sample solution is introduced from the injection section into the nanosize channel by capillary action.

27. The sample treatment apparatus according to claim 23, wherein one of the paired introducing electrodes that apply a voltage to the sample solution is arranged in the injection section, and the other is arranged in the nanosize channel, and
 an electric field is generated between the paired introducing electrodes to introduce the sample solution from the injection section into the nanosize channel.

28. The sample treatment apparatus according to claim 23, wherein the injection section has a cross-sectional size of micrometer order.

29. The sample treatment apparatus according to claim 23, wherein the voltage is an AC voltage.

30. The sample treatment apparatus according to claim 23, wherein the molecule separation circuit comprises:
 a predetermined electrode formed of an electrode pair provided on a nanosize channel side or a common electrode,
 a plurality of outlet electrodes provided at the respective plurality of branching channels,
 a voltage application section that applies a voltage to the predetermined electrode pair or to the predetermined electrode and one of the plurality of outlet electrodes, and
 a switching section that selects i) the predetermined electrode pair or ii) the pair of the predetermined electrode and one of the plurality of outlet electrodes, and
 the arithmetic processing circuit selects the pair based on information on the measured impedance value, and controls the molecule separation circuit in such a manner that the voltage is applied to the determined pair.

31. The sample treatment apparatus according to claim 23, wherein a plurality of electrode pairs are provided in the nanosize channel and arranged at predetermined intervals,
 the measurement circuit measures the impedance when the molecule passes through each of the electrode pairs, and
 the arithmetic processing circuit calculates a migration speed of the molecule based on a difference in a time when the impedance value is measured, and controls a timing for applying the voltage based on the calculated migration speed of the molecule.

32. The sample treatment apparatus according to claim 29, wherein the channel device is formed of a hydrophilic insulator material, and
 the sample solution is introduced from the injection section into the nanosize channel by capillary action.

33. The sample treatment apparatus according to claim 29, wherein one of the paired introducing electrodes that apply a voltage to the sample solution is arranged in the injection section, and the other is arranged in the nanosize channel, and
 an electric field is generated between the paired introducing electrodes to introduce the sample solution from the injection section into the nanosize channel.

34. The sample treatment apparatus according to claim 29, wherein the injection section and the plurality of output sections each have a cross-sectional size of micrometer order.

35. A sample treatment apparatus comprising:
 a channel device comprising an injection section from which a sample solution is injected and a nanosize channel having a cross section of a nanometer order size and through which a molecule contained in the sample solution is allowed to migrate;
 an AC power source that applies an AC voltage to between electrodes of an electrode pair installed in the nanosize channel, with at least a frequency of the AC power source varied;
 a measurement circuit which retains the molecule between the paired electrodes and changes an environment of the molecule and which measures impedance when the AC voltage is applied to between the electrodes, with the frequency of the AC power source varied; and
 an arithmetic processing circuit that measures a conformation of the molecule and a dynamic change therein based on the impedance value measured by the measurement circuit,
 wherein in the channel device, the electrode pair is covered with an insulator material so as not to contact the sample solution flowing through the nanosize channel, and a portion of the nanosize channel in which the electrode pair is arranged is configured to be smaller in width than the entire nanosize channel except for the portion in which the electrode pair is arranged.

36. The sample treatment apparatus according to claim 35, wherein a maximum value of a voltage to be applied by the AC power source to the paired electrodes in the nanosize channel is variable, the measurement circuit measures the impedance with the frequency and maximum voltage value of the AC power source varied, and the arithmetic processing circuit senses the conformation of the molecule and the dynamic change therein based on a change in the measured impedance when the frequency and the maximum voltage value are changed.

* * * * *